US005770369A

United States Patent [19]

Meade et al.

[11] Patent Number: 5,770,369
[45] Date of Patent: Jun. 23, 1998

[54] NUCLEIC ACID MEDIATED ELECTRON TRANSFER

[75] Inventors: Thomas J. Meade, Altadena; Jon Faiz Kayyem, Pasadena; Scott E. Fraser, Newport Beach, all of Calif.

[73] Assignee: California Institute of Technology, Pasadena, Calif.

[21] Appl. No.: 660,534

[22] Filed: Jun. 7, 1996

Related U.S. Application Data

[63] Continuation of Ser. No. 475,051, Jun. 7, 1995, which is a continuation of Ser. No. 166,036, Dec. 10, 1993, Pat. No. 5,591,578.

[51] Int. Cl.[6] .............................. C12Q 1/68; C12Q 1/70; C12P 19/34; C07H 21/04
[52] U.S. Cl. ................................. 435/6; 435/5; 435/91.2; 435/91.1; 435/287.2; 536/24.3; 536/25.3; 536/26.6; 536/24.33; 536/23.1
[58] Field of Search .................................. 435/6, 5, 91.2, 435/91.1, 287.2; 536/24.3, 25.3, 26.6, 23.1

[56] References Cited

U.S. PATENT DOCUMENTS

| | | |
|---|---|---|
| 4,707,352 | 11/1987 | Stavrianopoulos . |
| 4,711,955 | 12/1987 | Ward et al. . |
| 4,755,458 | 7/1988 | Rabbani et al. . |
| 4,849,513 | 7/1989 | Smith et al. . |
| 4,868,103 | 9/1989 | Stavrianopoulos et al. . |
| 4,894,325 | 1/1990 | Englehardt et al. . |
| 4,943,523 | 7/1990 | Stavrianopoulos . |
| 4,952,685 | 8/1990 | Stavrianopoulos . |
| 4,994,373 | 2/1991 | Stavrianopoulos . |
| 5,002,885 | 3/1991 | Stavrianopoulos . |
| 5,013,831 | 5/1991 | Stavrianopoulos . |
| 5,082,830 | 1/1992 | Brakel et al. . |
| 5,175,269 | 12/1992 | Stavrianopoulos . |
| 5,241,060 | 8/1993 | Englehardt et al. . |
| 5,278,043 | 1/1994 | Bannworth et al. ..................... 536/557 |
| 5,312,527 | 5/1994 | Mikkelsen et al. ................ 204/153.12 |
| 5,328,824 | 7/1994 | Ward et al. . |
| 5,449,767 | 9/1995 | Ward et al. . |
| 5,476,928 | 12/1995 | Ward et al. . |
| 5,495,908 | 3/1996 | Fawcett et al. ...................... 435/287.2 |
| 5,565,552 | 10/1996 | Magda et al. ............................. 534/11 |
| 5,573,906 | 11/1996 | Bannwarth et al. ........................ 435/6 |

FOREIGN PATENT DOCUMENTS

| | | |
|---|---|---|
| 2090904 | 9/1993 | Canada . |
| 0 063879 | 11/1982 | European Pat. Off. . |
| 0 234938 | 2/1987 | European Pat. Off. . |
| 0 229 943 | 7/1987 | European Pat. Off. . |
| 0229943 | 7/1987 | European Pat. Off. . |
| 0599337 | 1/1994 | European Pat. Off. . |
| 63-238168 | 10/1988 | Japan . |
| WO 9210757 | 6/1992 | WIPO . |
| WO 9310267 | 5/1993 | WIPO . |
| WO 9515971 | 6/1995 | WIPO . |

OTHER PUBLICATIONS

Baum, R. M., "Views on Biological, Long–Range Electron Transfer Stir Debate", C&EN, pp. 20–23 (Feb. 22, 1993).

Bechtold, R., et al., "Ruthenium–Modified Horse Heart Cytochrome c: Effect of pH and Ligation on the Rate of Intramolecular Electron Transfer between Ruthenium(II) and Heme(III)", J. Phys. Chem., 90(16):3800–3804 (1986).

Farver, O., et al., "Long–range intramolecular electron transfer in azurins", Proc. Natl. Acad. Sci. USA, 86:6968–6972 (1989).

Bowler, B. E., et al., "Long–Range Electron Transfer in Donor (Spacer) Acceptor Molecules and Proteins", Progress in Inorganic Chemistry: Bioinorganic Chemistry, 38:259–322 (1990).

Brun, A. M., et al., "Photochemistry of Intercalated Quaternary Diazaaromatic Salts", J. Am. Chem. Soc., 113:8153–8159 (1991).

Chang, I–Jy, et al., "High–Driving–Force Electron Transfer in Metalloproteins: Intramolecular Oxidation of Ferrocytochrome c by Ru(2,2'–bpy)$_2$(im) (His–33)$^{3+}$", J. Am. Chem. Soc., 113:7056–7057 (1991).

Davis, L. M., et al., "Electron Donor Properties of the Antitumour Drug Amsacrine as Studied by Fluorescence Quenching of DNA–Bound Ethidium", Chem.–Biol. Interactions, 62:45–58 (1987).

Degani, Y., et al., "Electrical Communication between Redox Centers of Glucose Oxidase and Electrodes via Electrostatically and Covalently Bound Redox Polymers", J. Am. Chem. Soc., 111:2357–2358 (1989).

Degani, Y., et al., "Direct Electrical Communication between Chemically Modified Enzymes and Metal Electrodes. 1. Electron Transfer from Glucose Oxidase to Metal Electrodes via Electron Relays, Bound Covalently to the Enzyme", J. Phys. Chem., 91(6):1285–1288 (1987).

Dreyer, G. B., et al., "Sequence–specific cleavage of single–stranded DNA: Oligodeoxynucleotide–EDTA$\flat$Fe(II)", Proc. Natl. Acad. Sci. USA, 82:968–972 (1985).

(List continued on next page.)

Primary Examiner—W. Gary Jones
Assistant Examiner—Dianne Rees
Attorney, Agent, or Firm—Flehr Hohbach Test Albritton & Herbert LLP; Richard F. Trecartin; Robin M. Silva

[57] ABSTRACT

The present invention provides for the selective covalent modification of nucleic acids with redox active moieties such as transition metal complexes. Electron donor and electron acceptor moieties are covalently bound to the ribose-phosphate backbone of a nucleic acid at predetermined positions. The resulting complexes represent a series of new derivatives that are bimolecular templates capable of transferring electrons over very large distances at extremely fast rates. These complexes possess unique structural features which enable the use of an entirely new class of bioconductors and photoactive probes.

27 Claims, 8 Drawing Sheets

OTHER PUBLICATIONS

Durham, B., et al., "Photoinduced Electron–Transfer Kinetics of Singly Labeled Ruthenium Bis(bipyridin) Dicarboxybipyridine Cytochrome c Derivatives", Biochemistry, 28:8659–8665 (1989).

Elias, H., et al., "Electron–Transfer Kinetics of Zn–Substituted Cytochrome c and Its Ru(NH$_3$)$_5$(Histidine–33) Derivative", J. Am. Chem. Soc., 110:429–434 (1988).

Fox, L. S., et al., "Gaussian Free–Energy Dependence of Electron–Transfer Rates in Iridium Complexes", Science, 247:1069–1071 (1990).

Fox, M. A., et al., "Light–Harvesting Polymer Systems", C&EN, pp. 38–48 (Mar. 15, 1993). vol. # not relevant.

Francois, J–C., et al., "Periodic Cleavage of Poly(dA) by Oligothymidylates Covalently Linked to the 1,10–Phenanthroline–Copper Complex", Biochemistry, 27:2272–2276 (1988).

Friedman, A. E., et al., "Molecular 'Light Switch' for DNA: Ru(bpy)$_2$(dpP$^z$)$^{2+}$", J. Am. Chem. Soc., 112:4960–4962 (1990).

Fromherz, P., et al., "Photoinduced Electron Transfer in DNA Matrix from Intercalated Ethidium to Condensed Methylviologen", J. Am. Chem. Soc., 108:5361–5362 (1986).

Gregg, B. A., et al., "Redox Polymer Films Containing Enzymes. 1. A Redox–Conducting Epoxy Cement: Synthesis, Characterization, and Electrocatalytic Oxidation of Hydroquinone", J. Phys. Chem., 95:5970–5975 (1991).

Heller, A., et al., "Amperometric biosensors based on three–dimensional hydrogel–forming epoxy networks", Sensors and Actuators, 13–14:180–183 (1993).

Heller, A., "Electrical Wiring of Redox Enzymes", Acc. Chem. Res., 23:128–134 (1990).

Meade. T. J., "Driving–Force Effects on the Rate of Long–Range Electron Transfer in Ruthenium–Modified Cytochrome c", J. Am. Chem. Soc., 111:4353–4356 (1989).

Murphy, C. J., et al., "Long–Range Photoinduced Electron Transfer Through a DNA Helix", Science, 262:1025–1029 (1993).

Orellana, G., et al., "Photoinduced Electron Transfer Quenching of Excited Ru(II) Polypyridyls Bound to DNA: The Role of the Nucleic Acid Double Helix", Photochemistry and Photobiology, 54(4):499–509 (1991).

Purugganan, M. D., et al., Accelerated Electron Transfer Between Metal Complexes Mediated by DNA, Science, 241:1645–1649 (1988).

Ho "DNA–Mediated Electron Transfer and Application to 'Biochip' Development," Abstract. Office of Naval Research (Report Date: Jul. 25, 1991) 1–4, RR04106.

Risser, S. M., et al., "Electron Transfer in DNA: Predictions of Exponential Growth and Decay of Coupling with Donor–Acceptor Distance", J. Am. Chem. Soc., 115(6):2508–2510 (1993).

Satyanarayana, S., et al., "Neither þ– nor þ–Tris(phenanthroline)ruthenium(II) Binds to DNA by Classical Intercalation", Biochemistry, 31(39):9319–9324 (1992).

Schuhmann, W., et al., "Electron Transfer between Glucose Oxidase and Electrodes via Redox Mediators Bound with Flexible Chains to the Enzyme Surface", J. Am. Chem. Soc., 113:1394–1397 (1991).

Strobel, S. A., et al., "Site–Specific Cleavage of a Yeast Chromosome by Oligonucleotide–Directed Triple–Helix Formation", Science, 249:73–75 (1990).

Telser, J., et al., "DNA Duplexes Covalently Labeled at Two Sites: Synthesis and Characterization by Steady–State and Time–Resolved Optical Spectroscopies", J. Am. Chem. Soc., 111:7226–7232 (1989).

Telser, J., et al., "DNA Oligomers and Duplexes Containing a Covalently Attached Derivative of Tris(2,2'–bipyridine)ruthenium(II): Synthesis and Characterization by Thermodynamic and Optical Spectroscopic Measurements", J. Am. Chem. Soc., 111:7221–7226 (1989).

Turro, N. J., et al., "Molecular Recognition and Chemistry in Restricted Reaction Spaces. Photophysics and Photoinduced Electron Transfer on the Surfaces of Micelles, Dendrimers, and DNA", Acc. Chem. Res., 24:332–340 (1991).

Winkler, J. R., et al., "Electron Transfer in Ruthenium–Modified Proteins", Chem. Rev., 92:369–379 (1992).

Murphy, C.J. et al., "Long–Range Photoinduced Electron Transfer Through a DNA Helix", Science, 262:1025–1029 (1993).

Boguslavsky, L. et al., "Applications of redox polymers in biosensors", Solid State Ionics, 60:189–197 (1993).

Millan, K.M. and Mikkelsen, S.R., "Sequence–Selective Biosensor for DNA Based on Electroactive Hybridization Indicators", Anal. Chem., 65: 2317–2323 (1993).

Cantor, C.R. et al., "Report on the Sequencing by Hybridization Workshop", Genomics, 13: 1378–1383 (1992).

Database WPI, Derwent Publications Ltd., London, GB; AN 88–320199 & JP, A, 53 238 166 (Mitsubishi Denki KK), 4 Oct. 1988.

Turro, N. , et al. "Photoelectron Transfer Between Molecules Adsorbed in Restricted Spaces." Photochem. Convers. Storage Sol. Energy, Proc. Int. Conf., 8th 1990, pp. 121–139. vol. # not relevant.

Degani et al., "Direct Electrical Communication between Chemically Modified Enzymes and Metal Electrodes. 2. Methods for Bonding Electron–Transfer Relays to Glucose Oxidase and D–Amino–Acid Oxidase," J. Am. Chem. Soc. 110:2615–2620 (1988).

Meade et al. , "Electron Transfer through DNA: Site–Specific Modification of Duplex DNA with Ruthenium Donors and Acceptors," Angew Chem. Int. Ed. Engl. 34:352 (1995).

Chidsey, C.E.D., et al., "Free Energy and Temperature Dependence of Electron Transfer at the Metal Electrolyte Interface", Science, 251:919–923 (1991).

Boguslavsky, L, et al., "Applications of redox polymers in biosensors", Solid State Ionics, 60:189–197(1993).

Deinhammer, R.S., et al., "Electronchemical Oxidation of Amine–containing compounds: A Route to the Surface Modification of glassy carbon electrodes", Langmuir, 10:1306–1313 (1994).

Gregg, B.A., et al., "Cross–linked redox gels containing glucose oxidase for amperometric biosensor applications", Anal. Chem., 62:258–263 (1990).

Heller, A., et al., "Amperometric biosensors based on three dimensional hydrogel–forming epoxy networks", Sensors and Actuators, 13–14:180–183(1993).

Lenhard, J.R., et al., "Part VII Covalent Bonding of a Reversible Electrode Reactanbt to Pt Electrodes Using an organosilane Reagent" J. Electronal. Chem., 78:195–201 (1977).

Millan, K.M., et al., "Covalent Immobilization of DNA onto Glassy Carbon Electrodes", Electroanalysis, 4:929–932, (1992).

Miller, C., "Absorbed p–Hydroxy Thiol Monolayers on Gold Electrodes: Evidence for Electron Tunneling to Redox Species in Solution", J. Phys. Chem., 95:877–886 (1991).

Hobbs et al., "Polynucleotides Containing 2'–Amino–2'deoxyribose and 2'–Azido–2'–deoxyriose," Biochemistry, 12(25):5138–5145 (1973).

Jenkins et al., "A Sequence–Specific Molecular Light Switch: Tebhering of an Oligonucleotide to a Dipyridophenazine Complex of Ruthenium (II)" J. Am. Chem. Soc., 114:8736–8738 (1992).

Kojima et al., "A DNA Probe of Ruthenium Bipyridine Complex Using Photocatalytic Activity," Chemistry Letter, 1889–1982 (1989).

Paterson, "Electric Genes: Current Flow in DNA Could Lead to Faster Genetic Testing," Scientific American, 33–34 (May 1995).

Clery, "DNA Goes Electric," Science, 267–1270 (Mar. 1995).

Mestel, "'Electron Highway' Points to Identity of DNA," New Scientist, p. 21 (4 Mar. 1995). volume # not relevant.

Lipkin "Identifying DNA by the Speed of Electrons," Science News, 147(8)117 (Feb. 25, 1995).

"Biotechnology and Genetics: Genetic Screening Integrated Circuit," The Economist, (Feb. 25–Mar. 3, 1995). volume #'s page #'s not relevant.

Hsung, et al., "Synthesis and Characterization of Unsymmetric Ferrocene–Terminated Phenylethynyl Oligomers", Organometallics 14:4808–4815 (1995).

Weber, et al., "Voltammetry of Redox–Active Groups Irreversibly Adsorbed onto Electrodes. Treatment Using the Marcus Relation between Rate and Overpotential", Anal. Chem. 66:3164–3172 (1994).

Millan, et al., "Sequence–Selective Biosensor for DNA Based on Electroactive Hybridization Indicators", Anal. Chem. 65:2317–2323 (1993).

Tour, et al., "Self–Assembled Monolayers and Multilayers of Conjugated Thiols, p–p–Dithiols, and Thioacetyl–Containing Adsorbates. Understanding Attachments between Potential Molecular Wires and Gold Surfaces", J. Am. Chem. Soc. 117:9529–9534 (1995).

Bumm, et al., "Are Single Molecular Wires Conducting?", Science 271:1705–1707 (1996).

Chidsey, "Free Energy and Temperature Dependence of Electron Transfer at the Metal–Electrolyte Interface", Science 251:919–922 (1991).

Maskos, et al., "Oligonucleotide hybridisations on glass supports: a novel linker for oligonucleotide synthesis and hybridisation properties of oligonucleotides synthesised in situ", Nucleic Acids Research 20(7):1679–1684 (1992).

Southern, et al., "Arrays of complementary oligonucleotides for analysing the hybridisation behaviour of nucleic acids", Nucleic Acids Research 22(8):1368–1373 (1994).

Williams, et al., "Studies of oligonucleotide interactions by hybridisation to arrays: the influence of dangling ends on duplex yield", Nucleic Acids Research 22(8):1365–1367 (1994).

Chrisey, et al., "Covalent attachment of synthetic DNA to self–assembled monolayer films", Nucleic Acids Research 24(15):3031–3039 (1996).

Palecek, "From Polarography of DNA to Microanalysis with Nucleic Acid–Modified Electrodes", Electroanalysis 8(1):7–14 (1996).

Schreiber, et al., "Bis(purine) Complexes of trans–$a_2$P II: Preparatio Structures of Bis(9–methyladenine) and Mixed 9–Methyladenine, 9–Methylquanine Complexes and Chemistry Relevant to Metal–Modified Nuceolobase Triples and Quartets", J. Am. Chem. Soc. 118:4124–4132 (1996).

Tour, "Conjugated Macromolecules of Precise Length and Constitution. Organic Synthesis for the Construction of Nanoarchitectures", Chem. Rev. 96:537–553 (1996).

Schumm, et al., "Iterative Divergent/Convergent Approach to Linear Conjugated Oligomers by Successive Doubling of the Molecular Length: A Rapid Route to a 128 p–Long Potential Molecular Wire", Angew. Chem. Int. Ed. Engl. 33(11):1360–1363 (1994).

McGee, et al., "2'–Amino–2'–deoxyuridine via an Intramolecular Cyclization of a Trichloroacetimidate", J. Org. Chem. 61:781–785 (1996).

Millan, et al., "Voltammetric DNA Biosensor for Cystic Fibrosis Based on a Modified Carbon Paste Electrode", Anal. Chem. 66:2943–2948 (1994).

Lee, et al., "Direct Measurement of the Forces Between Complementary Strands of DNA", Science 266:771–773 (1994).

Xu, et al., "Immobilization and Hybridization of DNA on an Aluminum(III) Alkanebisphosphonate Thin Film with Electrogenerated Chemiluminescent Detection", J. Am. Chem. Soc. 117:2627–2631 (1995).

Yang, et al., "Growth and Characterization of Metal(II) Alkaneobisphosphonate Multilayer Thin Films on Gold Surfaces", J. Am. Chem. Soc. 115:11855–11862 (1993).

Xu, et al., "Immobilization of DNA on an Aluminum(III) alkaneobisphosphonate Thin Film with Electrogenerated Chemiluminescent Detection", J. Am. Chem. Soc. 116:8386–8387 (1994).

Chidsey, et al., "Coadsorption of Ferrocene–Terminated and Unsubstituted Alkanethiols on Gold Electroactive Self–Assembled Monolayers", J. Am. Chem. Soc. 112:4301–4306 (1990).

Hsung, et al., "Thiophenol Protecting Groups for the Palladium–Catalyzed Heck Reaction: Efficient Syntheses of Conjugated Arylthiols", Tetrahedron Letters 36(26):4525–4528 (1995).

Katritzky, et al., "Pyridylethylation—A New Protection Method for Active Hydrogen Compounds", Tetrahedron Letters 25(12):1223–1226 (1984).

Barisci, et al., "Conducting Polymer Sensors", TRIP 4(9):307–311 (1996).

Davis, et al., "Elements of biosensor construction", Enzyme Microb. Technol. 17:1030–1035 (1995).

Gardner, et al., "Application of conducting polymer technology in microsystems", Sensors and Actuators, A51:57–66 (1995).

Bidan, "Electroconducting conjugated polymers: new sensitive matrices to build up chemical or electrochemical sensors. A Review.", Sensors and Actuators B6:45–56 (1992).

Zhou, et al., "Fluorescent Chemosensors Based on Energy Migration in Conjugated Polymers: The Molecular Wire Approach to Increased Sensitivity", J. Am. Chem. Soc. 117:12593–12602 (1995).

Hegner, et al., "Immobilizing DNA on gold via thiol modification for atomic force microscopy imaging in buffer solutions", FEBS 336(3):452–456 (1993).

Hashimoto, et al., "Sequence–Specific Gene Detection with a Gold Electrode Modified with DNA Probes and an Electrochemically Active Dye", *Anal. Chem.* 66:3830–3833 (1994).

Su, et al., "Interfacial Nucleic Acid Hybridization Studied by Random Primer $^{32}$P Labelling and Liquid–Phase Acoustic Network Analysis", *Analytical Chemistry* 66(6):769–777 (1994).

Commerce Business Daily Issue of Sep. 26, 1996 PSA#1688.

Sigal et al., "A Self–Assembled Monolayer for the Binding and Study of Histidine–Tagged Proteins by Surface Plasmon Resonance," *Anal. Chem.* 68(3):490–497 (1996).

Heller et al., "Fluorescent Energy Transfer Oligonucleotide Probes," *Fed. Proc.* 46(6):1968 (1987) Abstract No. 248.

Mazzocchi, Ph.H. and G. Fritz, "Photolysis of N–(2–Methyl–2–Propenyl)phthalimide in Methanol. Evidence Supporting Radical–Radical Coupling of a Photochemically Generated Radical Ion Pair," *Journal of the American Chemical Society*, 108(18):5361–5362 (1986).

Rhodes, D. And A. Klug, "Helical Periodicity of DNA Determined by Enzyme Digestion," *Nature*, 286:573–578 (1980).

Tullius, T.D. and B.A. Dombroski, "Iron(II) EDTA Used to Measure the Helical Twist Along Any DNA Molecule," *Science*, 230:679–681 (1985).

FIG._1A
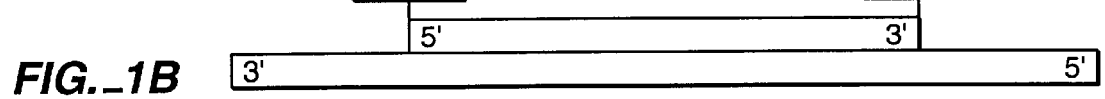
FIG._1B
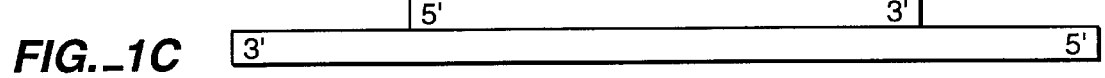
FIG._1C
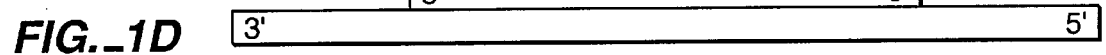
FIG._1D
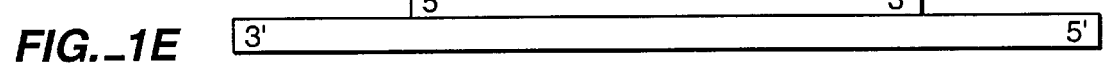
FIG._1E
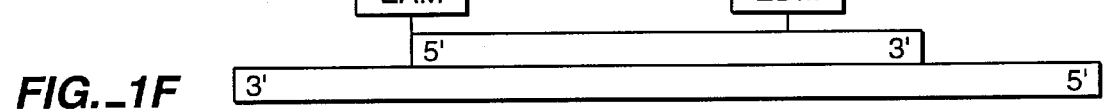
FIG._1F
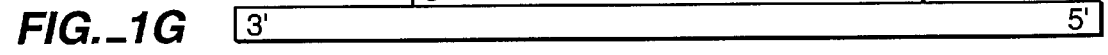
FIG._1G
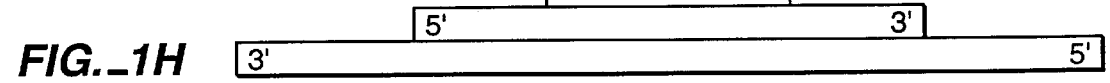
FIG._1H

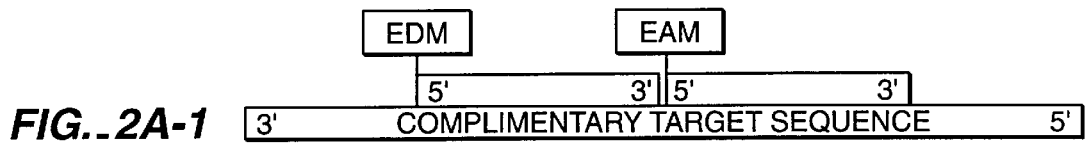
FIG._2A-1
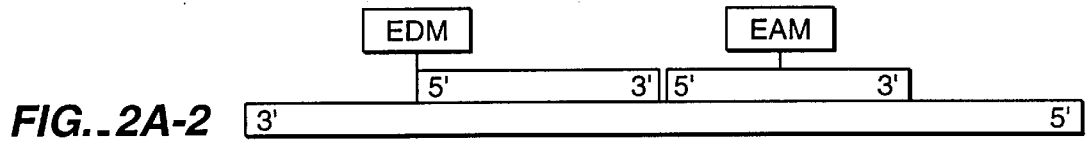
FIG._2A-2
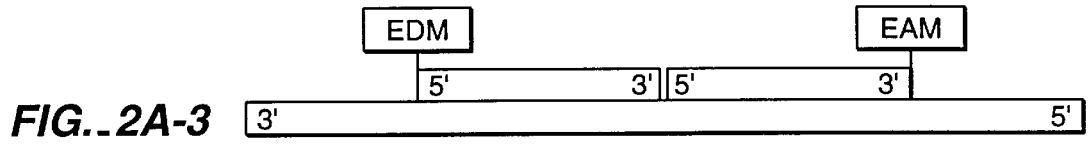
FIG._2A-3
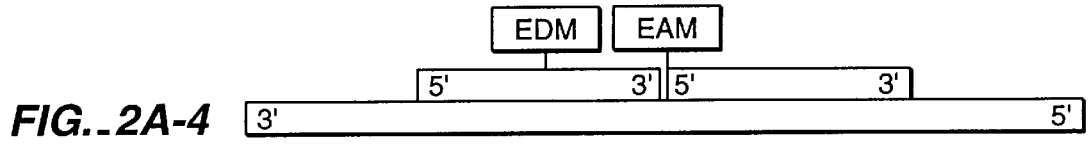
FIG._2A-4
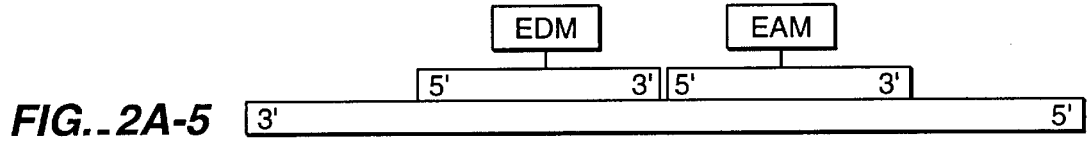
FIG._2A-5
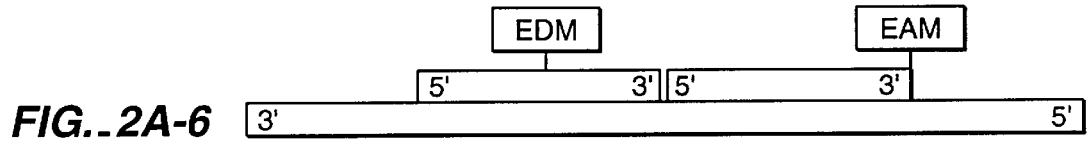
FIG._2A-6
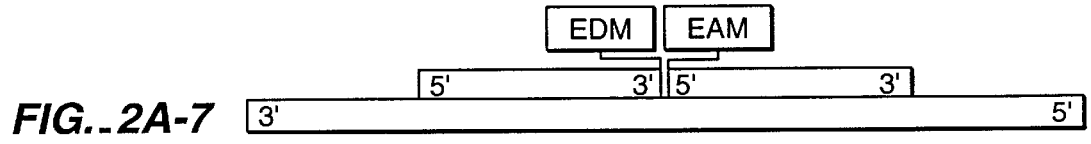
FIG._2A-7
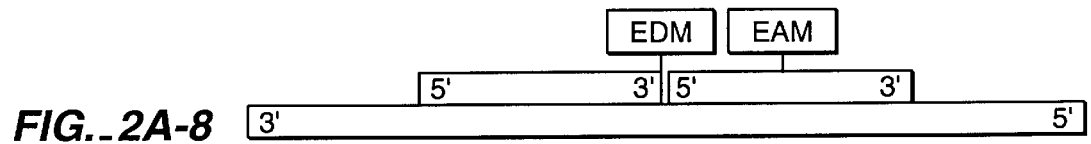
FIG._2A-8
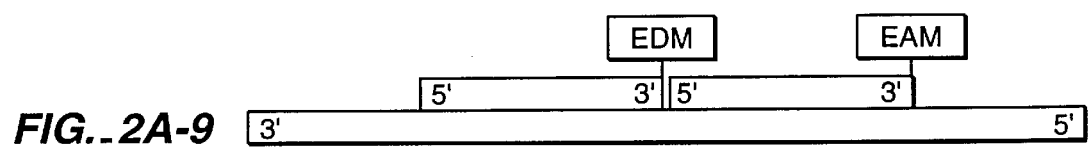
FIG._2A-9

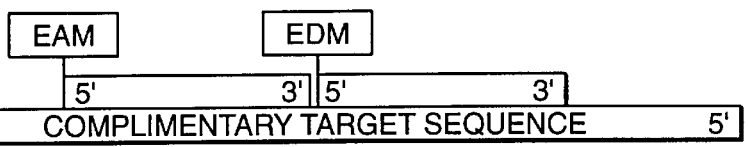
FIG._2B-1
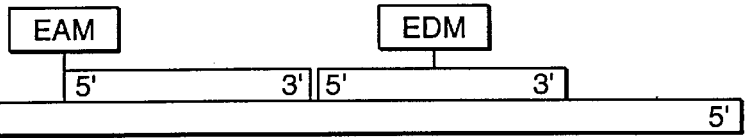
FIG._2B-2
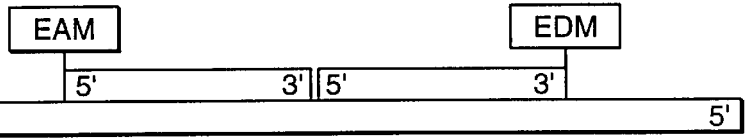
FIG._2B-3
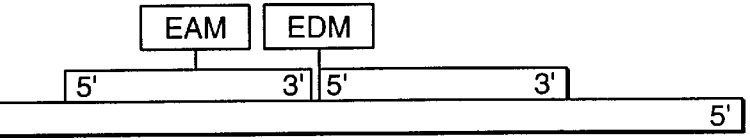
FIG._2B-4
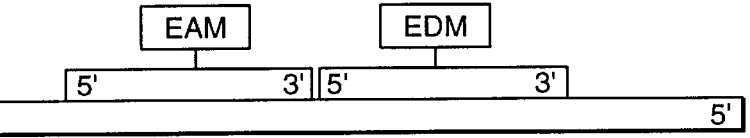
FIG._2B-5
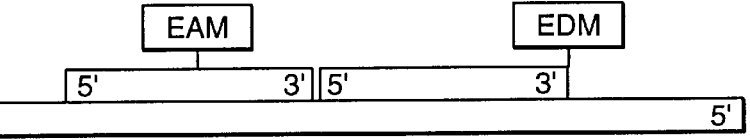
FIG._2B-6
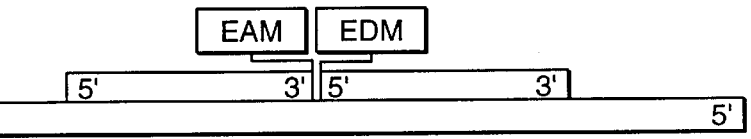
FIG._2B-7
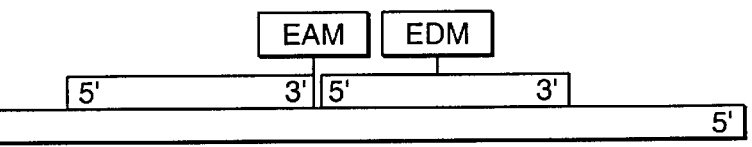
FIG._2B-8
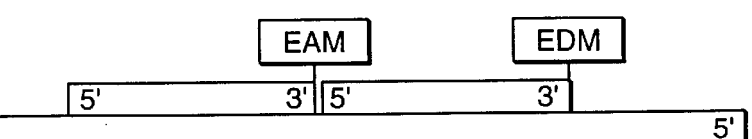
FIG._2B-9
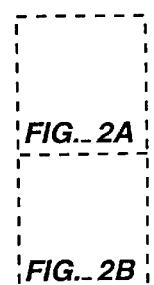
FIG._2

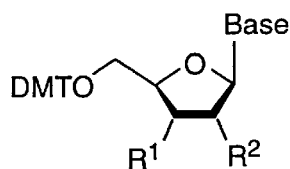
(I)   $R^1 = H$   $R^2 = NH_2$
(II)  $R^1 = NH_2$   $R^2 = H$
(III) $R^1 = NH_2$   $R^2 = OH$
(IV)  $R^1 = OH$   $R^2 = NH_2$
(Base) Adenine, guanine, cytosine, thymidine, uridine.
FIG._3
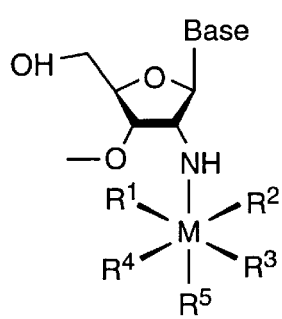
FIG._4A
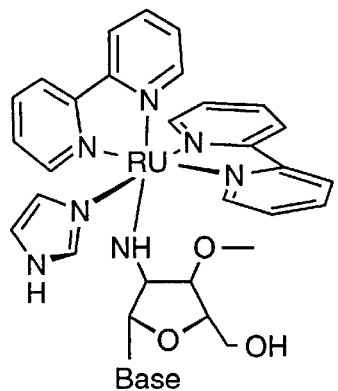
FIG._4B
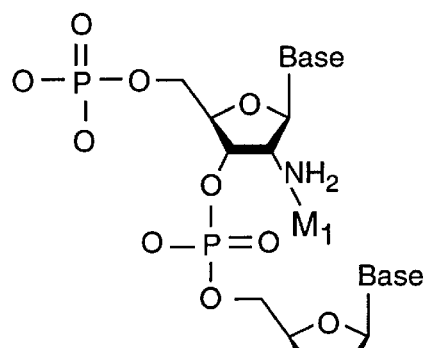
FIG._5

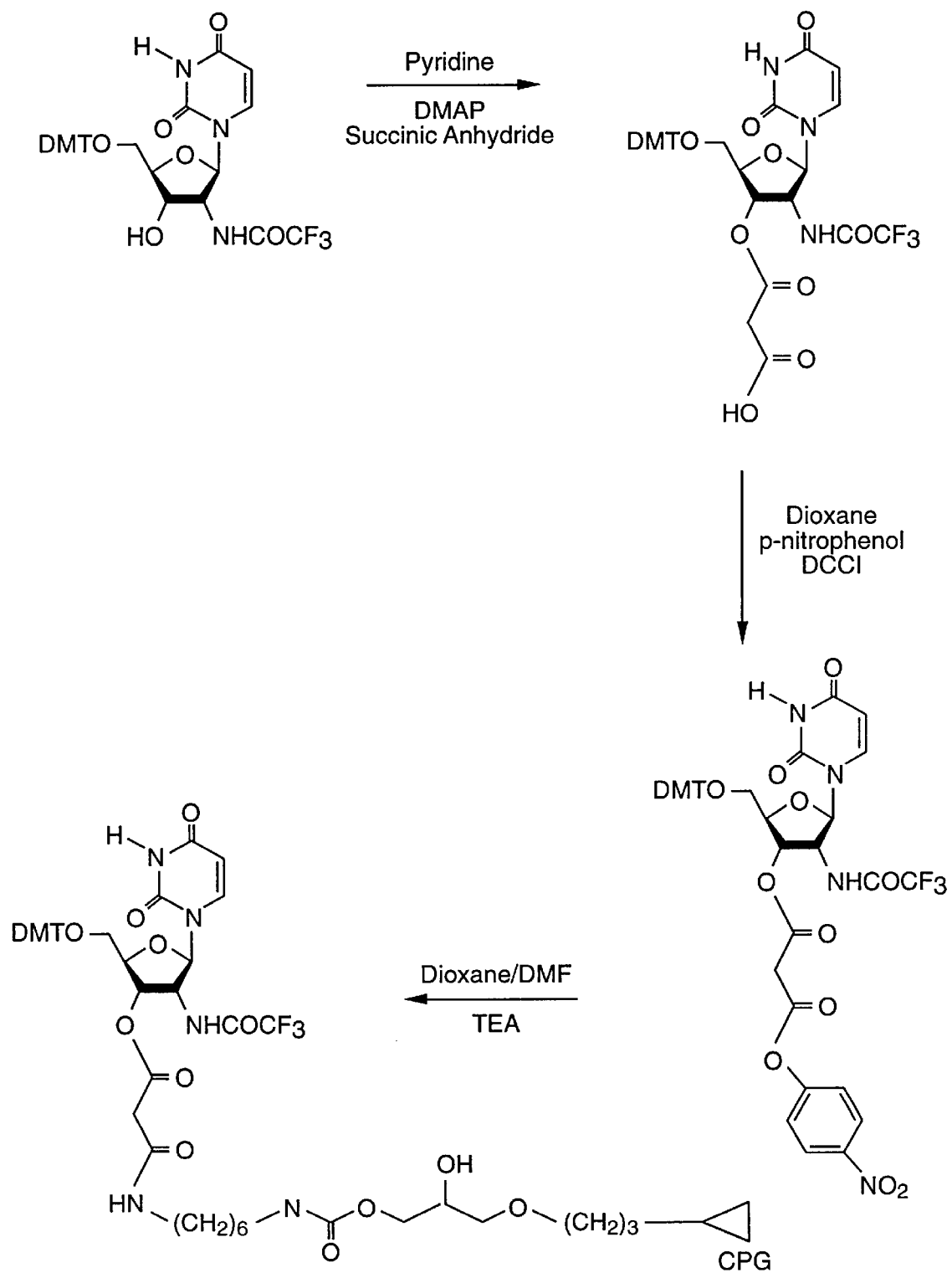
FIG._6A

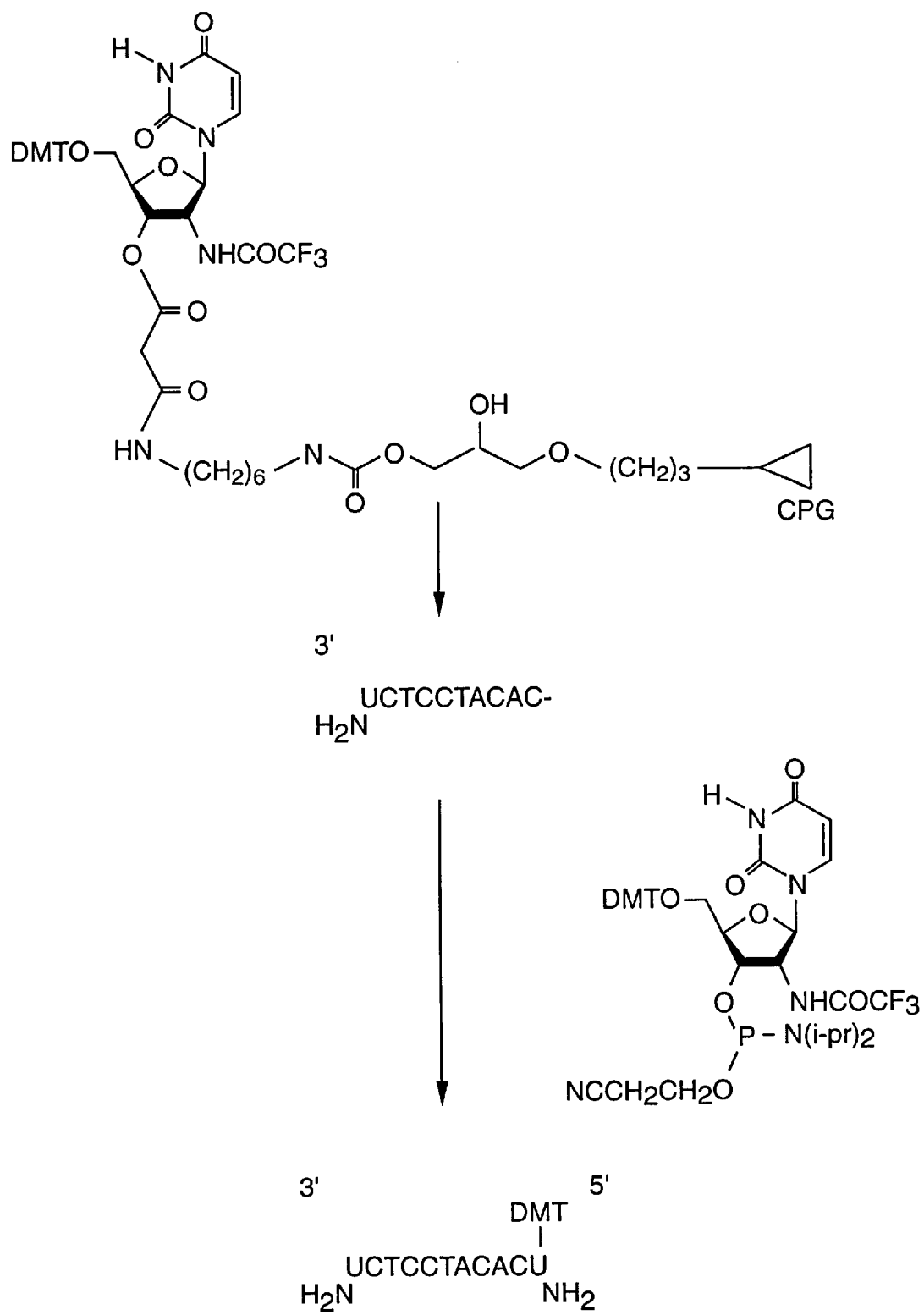
FIG._6B

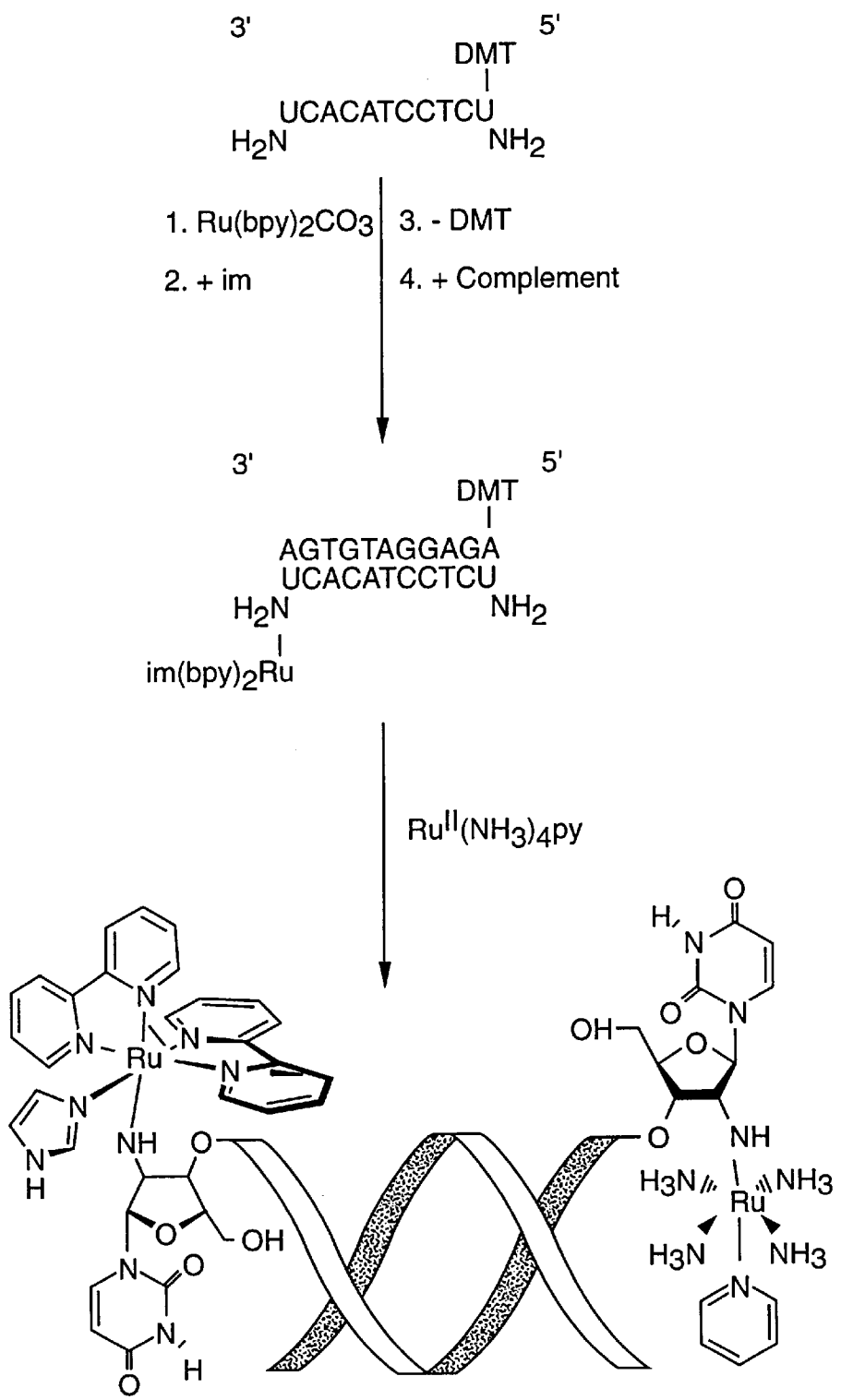
FIG._6C

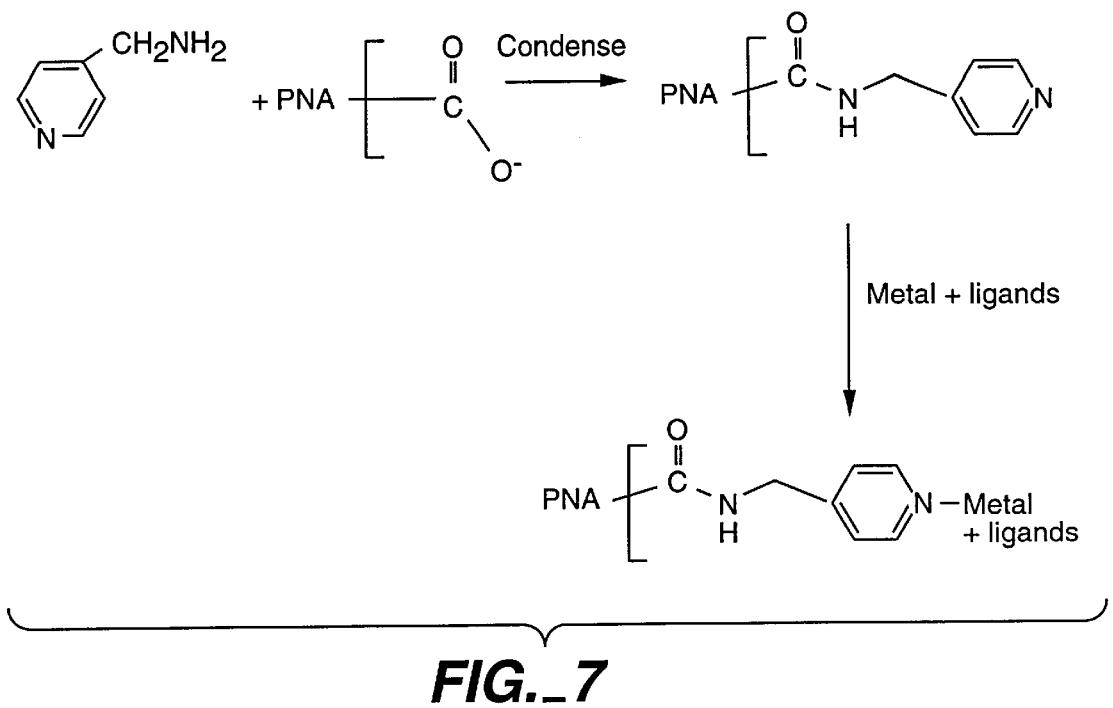
FIG._7
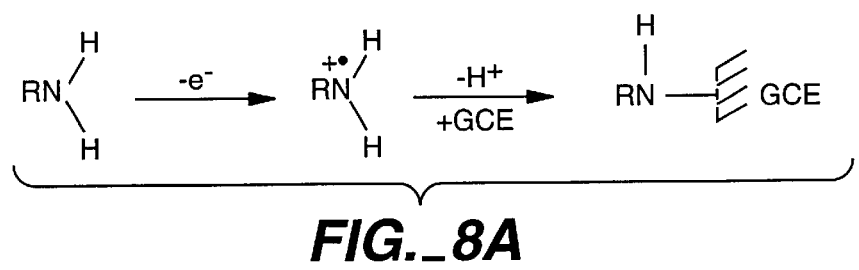
FIG._8A
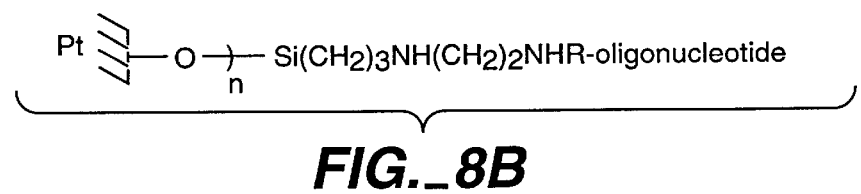
FIG._8B

NUCLEIC ACID MEDIATED ELECTRON TRANSFER

This is a continuing application under 35 U.S.C. 120/121 of U.S. patent application Ser. No. 08/475,051, filed Jun. 7, 1995, which is a continuing application under 35 U.S.C. 120/121 of U.S. patent application Ser. No. 08/166,036, filed Dec. 10, 1993 now U.S. Pat. No. 5,591,578.

FIELD OF THE INVENTION

The present invention is directed to electron transfer via nucleic acids. More particularly, the invention is directed to improvements in the site-selective modification of nucleic acids with electron transfer moieties.

BACKGROUND OF THE INVENTION

The detection of specific nucleic acid sequences is an important tool for diagnostic medicine and molecular biology research. Gene probe assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48–51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4:41–47 (1993)).

Specificity, in contrast, remains a problem in many currently available gene probe assays. The extent of molecular complementarity between probe and target defines the specificity of the interaction. Variations in the concentrations of probes, of targets and of salts in the hybridization medium, in the reaction temperature, and in the length of the probe may alter or influence the specificity of the probe/target interaction.

It may be possible under some limited circumstances to distinguish targets with perfect complementarity from targets with mismatches, although this is generally very difficult using traditional technology, since small variations in the reaction conditions will alter the hybridization. New experimental techniques for mismatch detection with standard probes include DNA ligation assays where single point mismatches prevent ligation and probe digestion assays in which mismatches create sites for probe cleavage.

Finally, the automation of gene probe assays remains an area in which current technologies are lacking. Such assays generally rely on the hybridization of a labelled probe to a target sequence followed by the separation of the unhybridized free probe. This separation is generally achieved by gel electrophoresis or solid phase capture and washing of the target DNA, and is generally quite difficult to automate easily.

The time consuming nature of these separation steps has led to two distinct avenues of development. One involves the development of high-speed, high-throughput automatable electrophoretic and other separation techniques. The other involves the development of non-separation homogeneous gene probe assays.

For example, Gen-Probe Inc., (San Diego, Calif.) has developed a homogeneous protection assay in which hybridized probes are protected from base hydrolysis, and thus are capable of subsequent chemiluminescence. (Okwumabua et al. Res. Microbiol. 143:183 (1992)). Unfortunately, the reliance of this approach on a chemiluminescent substrate known for high background photon emission suggests this assay will not have high specificity. EPO application number 86116652.8 describes an attempt to use non-radiative energy transfer from a donor probe to an acceptor probe as a homogeneous detection scheme. However, the fluorescence energy transfer is greatly influenced by both probe topology and topography, and the DNA target itself is capable of significant energy quenching, resulting in considerable variability. Therefore there is a need for DNA probes which are specific, capable of detecting target mismatches, and capable of being incorporated into an automated system for sequence identification.

As outlined above, molecular biology relies quite heavily on modified or labelled oligonucleotides for traditional gene probe assays (Oligonucleotide Synthesis: A Practical Approach. Gait et al., Ed., IRL Press: Oxford, UK, 1984; Oligonucleotides and Analogues: A Practical Approach. Ed. F. Eckstein, Oxford University Press, 1991). As a result, several techniques currently exist for the synthesis of tailored nucleic acid molecules. Since nucleic acids do not naturally contain functional groups to which molecules of interest may easily be attached covalently, methods have been developed which allow chemical modification at either of the terminal phosphates or at the heterocyclic bases (Dreyer et al. Proc. Natl. Acad. Sci. USA, 1985, 82:968).

For example, analogues of the common deoxyribo- and ribonucleosides which contain amino groups at the 2' or 3' position of the sugar can be made using established chemical techniques. (See Imazawa et al., J. Org. Chem., 1979, 44:2039; Imazawa et al., J. Org. Chem. 43(15):3044 (1978); Verheyden et al., J. Org. Chem. 36(2):250 (1971); Hobbs et al., J. Org. Chem. 42(4):714 (1977)). In addition, oligonucleotides may be synthesized with 2'-5' or 3'-5' phosphoamide linkages (Beaucage et al., Tetrahedron 49(10):1925 (1992); Letsinger, J. Org. Chem., 35:3800 (1970); Sawai, Chem. Left. 805 (1984); Oligonucleotides and Analogues: A Practical Approach, F. Eckstein, Ed. Oxford University Press (1991)).

The modification of nucleic acids has been done for two general reasons: to create nonradioactive DNA markers to serve as probes, and to use chemically modified DNA to obtain site-specific cleavage.

To this end, DNA may be labelled to serve as a probe by altering a nucleotide which then serves as a replacement analogue in the nick translational resynthesis of double stranded DNA. The chemically altered nucleotides may then provide reactive sites for the attachment of immunological or other labels such as biotin. (Gilliam et al., Anal. Biochem. 157:199 (1986)). Another example uses ruthenium derivatives which intercalate into DNA to produce photoluminescence under defined conditions. (Friedman et al., J. Am. Chem. Soc. 112:4960 (1990)).

In the second category, there are a number of examples of compounds covalently linked to DNA which subsequently cause DNA chain cleavage. For example 1,10-phenanthroline has been coupled to single-stranded oligothymidylate via a linker which results in the cleavage of poly-dA oligonucleotides in the presence of $Cu^{2+}$ and 3-mercaptopropionic acid (Francois et al., Biochemistry 27:2272 (1988)). Similar experiments have been done for EDTA[1]-Fe(II) (both for double stranded DNA (Boutorin et al., FEBS Left. 172:43–46 (1986)) and triplex DNA (Strobel et al., Science 249:73 (1990)), porphyrin-Fe(III) (Le Doan et al., Biochemistry 25:6736–6739 (1986)), and 1,10-phenanthronine-Cu(I) (Chen et al., Proc. Natl. Acad. Sci USA, 83:7147 (1985)), which all result in DNA chain cleavage in the presence of a reducing agent in aerated solutions. A similar example using porphyrins resulted in DNA strand cleavage, and base oxidation or cross-linking of the DNA under very specific conditions (Le Doan et al., Nucleic Acids Res. 15:8643 (1987)).

Other work has focused on chemical modification of heterocyclic bases. For example, the attachment of an inorganic coordination complex, Fe-EDTA, to a modified internal base resulted in cleavage of the DNA after hybridization in the presence of dioxygen (Dreyer et al., Proc. Natl. Acad. Sci. USA 82:968 (1985)). A ruthenium compound has been coupled successfully to an internal base in a DNA octomer, with retention of both the DNA hybridization capabilities as well as the spectroscopic properties of the ruthenium label (Telser et al., J. Am. Chem. Soc. 111:7221 (1989)). Other experiments have successfully added two separate spectroscopic labels to a single double-stranded DNA molecule (Telser et al., J. Am. Chem. Soc. 111:7226 (1989)).

The study of electron transfer reactions in proteins and DNA has also been explored in pursuit of systems which are capable of long distance electron transfer.

To this end, intramolecular electron transfer in protein-protein complexes, such as those found in photosynthetic proteins and proteins in the respiration pathway, has been shown to take place over appreciable distances in protein interiors at biologically significant rates (see Bowler et al., Progress in Inorganic Chemistry: Bioinorganic Chemistry, Vol. 38, Ed. Stephen J. Lippard (1990). In addition, the selective modification of metalloenzymes with transition metals has been accomplished and techniques to monitor electron transfer in these systems developed. For example, electron transfer proteins such as cytochrome c have been modified with ruthenium through attachment at several histidines and the rate of electron transfer from the heme $Fe^{2+}$ to the bound $Ru^{3+}$ measured. The results suggest that electron transfer "tunnel" pathways may exist. (Baum, Chemical & Engineering News, Feb. 22, 1993, pages 2023; see also Chang et al., J. Am. Chem. Soc. 113:7056 (1991)). In related work, the normal protein insulation, which protects the redox centers of an enzyme or protein from nondiscriminatory reactions with the exterior solvent, was "wired" to transform these systems from electrical insulators into electrical conductors (Heller, Acc. Chem. Res. 23:128 (1990)).

There are a few reports of photoinduced electron transfer in a DNA matrix. In these systems, the electron donors and acceptors are not covalently attached to the DNA, but randomly associated with the DNA, thus rendering the explicit elucidation and control of the donor-acceptor system difficult. For example, the intense fluorescence of certain quaternary diazoaromatic salts is quenched upon intercalation into DNA or upon exposure to individual mononucleotides, thus exhibiting electron donor processes within the DNA itself. (Brun et al., J. Am. Chem. Soc. 113:8153 (1991)).

Another example of the difficulty of determining the electron transfer mechanism is found in work done with some photoexcitable ruthenium compounds. Early work suggested that certain ruthenium compounds either randomly intercalate into the nucleotide bases, or bind to the helix surface. (Purugganan et al., Science 241:1645 (1988)). A recent reference indicates that certain ruthenium compounds do not intercalate into the DNA (Satyanarayana et al., Biochemistry 31(39):9319 (1992)); rather, they bind non-covalently to the surface of the DNA helix.

In these early experiments, various electron acceptor compounds, such as cobalt, chromium or rhodium compounds were added to certain DNA-associated ruthenium electron donor compounds. (Purugganan et al., Science 241:1645 (1988); Orellana et al., Photochem. Photobiol. 499:54 (1991); Brun et al., J. Am. Chem. Soc. 113:8153 (1991); Davis, Chem.-Biol. Interactions 62:45 (1987); Tomalia et al., Acc. Chem. Res., 24:332 (1991)). Upon addition of these various electron acceptor compounds, which randomly bind non-covalently to the helix, quenching of the photoexcited state through electron transfer was detected. The rate of quenching was dependent on both the individual electron donor and acceptor as well as their concentrations, thus revealing the process as bimolecular.

In one set of experiments, the authors postulate that the more mobile surface bound donor promotes electron transfer with greater efficiency than the intercalated species, and suggest that the sugar-phosphate backbone of DNA, and possibly the solvent medium surrounding the DNA, play a significant role in the electron transport. (Purugganan et al., Science 241:1645 (1988)). In other work, the authors stress the dependence of the rate on the mobility of the donor and acceptor and their local concentrations, and assign the role of the DNA to be primarily to facilitate an increase in local concentration of the donor and acceptor species on the helix. (Orellana et al., supra).

In another experiment, an electron donor was reportedly randomly intercalated into the stack of bases of DNA, while the acceptor was randomly associated with the surface of the DNA. The rate of electron transfer quenching indicated a close contact of the donor and the acceptor, and the system also exhibits enhancement of the rate of electron transfer with the addition of salt to the medium. (Fromherz et al., J. Am. Chem. Soc. 108:5361 (1986)).

In all of these experiments, the rate of electron transfer for non-covalently bound donors and acceptors is several orders of magnitude less than is seen in free solution.

An important stimulus for the development of long distance electron transfer systems is the creation of synthetic light harvesting systems. Work to date suggests that an artificial light harvesting system contains an energy transfer complex, an energy migration complex, an electron transfer complex and an electron migration complex (for a topical review of this area, see Chemical & Engineering News, Mar. 15, 1993, pages 38–48). Two types of molecules have been tried: a) long organic molecules, such as hydrocarbons with covalently attached electron transfer species, or DNA, with intercalated, partially intercalated or helix associated electron transfer species, and b) synthetic polymers.

The long organic molecules, while quite rigid, are influenced by a number of factors, which makes development difficult. These factors include the polarity and composition of the solvent, the orientation of the donor and acceptor groups, and the chemical character of either the covalent linkage or the association of the electron transfer species to the molecule.

The creation of acceptable polymer electron transfer systems has been difficult because the available polymers are too flexible, such that several modes of transfer occur. Polymers that are sufficiently rigid often significantly interfere with the electron transfer mechanism or are quite difficult to synthesize.

Thus the development of an electron transfer system which is sufficiently rigid, has covalently attached electron transfer species at defined intervals, is easy to synthesize and does not appreciably interfere with the electron transfer mechanism would be useful in the development of artificial light harvesting systems.

In conclusion, the random distribution and mobility of the electron donor and acceptor pairs, coupled with potential short distances between the donor and acceptor, the loose and presumably reversible association of the donors and acceptors, the reported dependence on solvent and broad putative electron pathways, and the disruption of the DNA structure of intercalated compounds rendering normal base pairing impossible all serve as pronounced limitations of long range electron transfer in a DNA matrix. Therefore, a method for the production of rigid, covalent attachment of electron donors and acceptors to provide minimal perturbations of the nucleic acid structure and retention of its ability to base pair normally, is desirable. The present invention serves to provide such a system, which allows the development of novel bioconductors and diagnostic probes.

SUMMARY OF THE INVENTION

The present invention provides for the modification of nucleic acids at specific sites with redox active moieties such as transition metal complexes. An electron donor and/or electron acceptor moiety are covalently bound at predetermined positions. The resulting complexes represent a series of new derivatives that are biomolecular templates capable of transferring electrons over very large distances at extremely fast rates. These complexes possess unique structural features which enable the use of an entirely new class of bioconductors and diagnostic probes.

Accordingly, it is an object of the invention to provide nucleic acids with electron transfer species covalently attached to a terminal base of the nucleic acid. It is a further object to provide nucleic acids with covalently attached organic electron transfer species, and modified nucleic acids attached to control pore glass.

BRIEF DESCRIPTION OF THE DRAWINGS

FIG. 1 illustrates all the possible orientations of electron donor (EDM) and electron acceptor (EAM) moieties on a single stranded nucleic acid.

FIG. 2 illustrates the possible orientations of electron transfer moieties EDM and EAM on two adjacent single stranded nucleic acids. These orientations also apply when the two probes are separated by an intervening sequence.

FIG. 3 illustrates a series of amino-modified nucleoside precursors prior to incorporation into an oligonucleotide.

FIG. 4A and 4B depict the structure of electron transfer moieties. FIG. 4A depicts the general formula of a representative class of electron donors and acceptors. FIG. 4B depicts a specific example of a ruthenium electron transfer moiety using bisbipyridine and imidazole as the ligands.

FIG. 5 is a schematic showing transition metals bound to the ribose-phosphate backbone in a variety of positions. M is a transition metal. $M_1$ is bound via an amine on the 2' carbon of the ribose; an electron must travel through 4 σ bonds to enter the pi-orbitals (the "pi-way") of the stacked bases. $M_2$ and $M_3$ are bound via a phosphoramide-type linkages, and electrons must travel through 7 σ bonds to enter the pi-way, respectively. $M_4$ is bound via an amine on the 3' carbon of the ribose, and an an electron traverses through 5 σ bonds.

FIGS. 6A, 6B and 6C depict the attachment of a 2'-amino-modified nucleoside to control pore glass (CPG) and the formation of a single stranded nucleic acid with elongation and attachment of transition metal complexes as the exemplified electron transfer species. The experimental conditions are outlined in Example 9. FIG. 6A depicts the formation of 2'-amino-2'-deoxyuridine derivatized to control pore glass (CPG). 2'-amino modified uridine is depicted, although any base may be used. As is known in the art, phosphoramidite nucleosides are added to the derivatized nucleoside, after removal of the DMT protecting group, as generally depicted in FIG. 6B, using the UCTCCTACAC sequence as an example. The addition of a 5' terminal phosphoramidite 2-amino-deoxyuridine, with a DMT protecting group, results in a single stranded nucleic acid containing a 3' and 5' 2'-amino modified nucleoside. FIG. 6C depicts the addition of the electron transfer species, exemplified by two ruthenium transition metal complexes, im(bpy)$_2$Ru and Ru(II)(NH$_3$)$_4$py.

FIG. 7 depicts the addition of electron transfer moieties, exemplified by a transition metal complex, to the C-terminus of PNA. FIG. 9 attaches 4-aminomethylpyridine to the carboxy terminus, to form a ligand which may bind the metal at the nitrogen of the pyridine ring.

FIGS. 8A and 8B depicts attachment of the amino-modified nucleic acids of the invention to electrodes. (A) depicts the attachment to glassy carbon electrodes. R is the oligonucleotide, and GCE is a glassy carbon electrode. (B) depicts the attachment of the amino-modified nucleic acids of the invention to oxidized surfaces using silane reactions.

DETAILED DESCRIPTION

Unless otherwise stated, the term "nucleic acid" or "oligonucleotide" or grammatical equivalents herein means at least two nucleotides covalently linked together. A nucleic acid of the present invention will generally contain phosphodiester bonds, although in some cases, as outlined below, a nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). These modifications of the ribose-phosphate backbone may be done to facilitate the addition of electron transfer moieties, or to increase the stability and half-life of such molecules in physiological environments.

Particularly preferred are peptide nucleic acids (PNA). This backbone is substantially non-ionic under neutral conditions, in contrast to the highly charged phosphodiester backbone of naturally occurring nucleic acids. This results in two advantages. First, this backbone exhibits improved hybridization kinetics. PNAs have larger changes in the melting temperature (Tm) for mismatched versus perfectly matched basepairs. DNA and RNA typically exhibit a 2°–4° C. drop in Tm for an internal mismatch. With the non-ionic backbone of PNA, the drop is closer to 7°–9° C. This allows for better detection of mismatches. Similarly, due to their non-ionic nature, hybridization of the bases attached to these backbones is relatively insensitive to salt concentration. This is particularly advantageous in the systems of the present invention, as a reduced salt hybridization solution has a lower Faradaic current than a physiological salt solution (in the range of 150 mM).

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine and hypoxathanine, etc. In some instances, e.g. in the case of an "intervening nucleic acid", the term nucleic acid refers to one or more nucleosides. As used herein, the term "nucleoside" includes nucleotides.

The terms "electron donor moiety", "electron acceptor moiety", and "electron transfer moieties" or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention. Preferred electron transfer moieties include, but are not limited to, transition metal complexes, organic electron transfer moieties, and electrodes.

In a preferred embodiment, the electron transfer moieties are transition metal complexes. Transition metals are those whose atoms have an incomplete d shell of electrons. Suitable transition metals for use in the invention include, but are not limited to, cadmium (Cd), magnesium (Mg), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metal, the platinum metals (Ru, Rh, Pd, Os, Ir and Pt), along with Re, W, Mo and Tc, are preferred. Particularly preferred are ruthenium, rhenium, osmium, platinium and iron.

The transition metals are complexed with a variety of ligands to form suitable transition metal complexes, as is well known in the art. Suitable ligands include, but are not limited to, $-NH_2$; pyridine; pyrazine; isonicotinamide; imidazole; bipyridine and substituted derivative of bipyridine; phenanthrolines, particularly 1,10-phenanthroline (abbreviated phen) and substituted derivatives of phenanthrolines such as 4,7-dimethylphenanthroline; dipyridophenazine; 1,4,5,8,9,12-hexaazatriphenylene (abbreviated hat); 9,10-phenanthrenequinone diimine; 1,4,5,8-tetraazaphenanthrene (abbreviated tap); 1,4,8,11-tetra-azacyclotetradecane; diaminopyridine (abbreviated damp); porphyrins and substituted derivatives of the porphyrin family. A general formula that is representative of a class of donors and acceptors that may be employed is shown in FIG. 4A. The groups $R^1$, $R^2$, $R^3$, $R^4$, and $R^5$ may be any coordinating ligand that is capable of covalently binding to the chosen metal and may include any of the above ligands. The structure of a ruthenium electron transfer species using bisbipyridine and imidazole as the ligands is shown in FIG. 4B. Specific examples of useful electron transfer complexes include, but are not limited to, those shown in Table 1.

TABLE 1

| Donors | Acceptors |
|---|---|
| Ru(bpy)$_2$im-NH$_2$—U | Ru(NH$_3$)$_5$—NH$_2$—U |
| Ru(bpy)$_2$im-NH$_2$—U | Ru(NH$_3$)$_4$py-NH$_2$—U |
| Ru(bpy)$_2$im-NH$_2$—U | Ru(NH$_3$)$_4$im-NH$_2$—U |
| trans-Ru(cyclam)py | |

Where:
Ru = ruthenium
byp = bisbipyridine
im = imidazole
py = pyridine
cyclam = 1,4,8,11-tetra-azacyclotetradecane Other suitable moieties include bis(phenanthroline) (dipyridophenazine)Ru(II) (abbreviated [Ru(phen)$_2$dppz]$^{+2}$); bis(9,10-phenthrenequinone diimine) (phenanthroline)Rh(III), abbreviated [Rh(phi)$_2$phen]$^{+3}$; tris (phenanthroline)Ru(II) (abbreviated [Ru(o-phen)$_3$]$^{+2}$), Co(phen)$_3$$^{+3}$, Co(bpy)$_3$$^{+3}$; Rh(phen)$_3$$^{+3}$; Cr(phen)$_3$$^{+3}$; Ru(bpy)$_2$(dppz)$^{+2}$; and Ru(bpy)$_3$$^{+2}$.

In addition to transition metal complexes, other organic electron donors and acceptors may be covalently attached to the nucleic acid for use in the invention. These organic molecules include, but are not limited to, riboflavin, xanthene dyes, azine dyes, acridine orange, N,N'-dimethyl-2,7-diazapyrenium dichloride (DAP$^{2+}$), methylviologen, ethidium bromide, quinones such as N,N'-terminal dimethylanthra(2,1,9-def. 6,5,10-d'e'f')diisoquinoline dichloride (ADIQ$^{2+}$); porphyrins ([mesotetrakis(N-methyl-x-pyridinium)porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5, 5',7,7'-tetrasulfonic acid, indigo-5,5',7-trisulfonic acid; phenosafranine, indigo-5-monosulfonic acid; safranine T; bis(dimethylglyoximato)-iron(II) chloride; induline scarlet, neutral red, and subsitituted derivatives of these compounds.

In one embodiment, the electron donors and acceptors are redox proteins as are known in the art. However, redox proteins in many embodiments are not preferred.

In a particularly preferred embodiment, an electron transfer moiety comprises an solid support such as an electrode to which the nucleic acid is attached, covalently or otherwise. That is, the electrode serves as either the electron donor or acceptor, as is more fully described below. The techniques used in this embodiment are analogous to the wiring of proteins to an electrode except that the nucleic acids of the present invention are used rather than a redox protein (see for example Gregg et al., J. Phys. Chem. 95:5970 (1991); Heller et al., Sensors and Actuators R., 13–14:180 (1993); and Pishko et al., Anal. Chem., 63:2268 (1991)).

Electrode attachment is utilized in initiating electron transfer via an applied potential and for electronic methods of electron transfer monitoring.

In a preferred embodiment, electron transport between the electrode and the nucleic acid can be indirect, utilizing electron transport mediators which are free in solution or imbedded in a gel or polymer to provide a type of electronic coupling between the electrode and the nucleic acids. In a preferred embodiment, the electron transfer moiety-modified nucleic acids of the invention are attached via such a matrix. Matrix attachment has several advantages for use in a nucleic acid gene sensor. Because of the 3-dimensional nature of the polymer, large numbers of modified nucleic acid probes can be attached to a small surface area of electrode. Using a highly porous "hydrogel," rates of nucleic acid hybridization can be quite high, nearly matching that of nucleic acid in solution.

For example, polymers with covalently attached redox molecules behave as highly effective electron transfer mediators. Siloxane and ethylene oxide polymers, modified with ferrocene molecules, demonstrated electron transfer between enzymes and an electrode; for example, flexible siloxane and ethylene oxide polymers covalently attached to ferrocene or Os(bpy)$_2$ have been shown to be highly effective redox polymers for mediating electron transfer from several enzymes to an electrode. (see Boguslavsky et al., Solid State Ionics, V. 60, p. 189, (1993)). Similarly, a redox-conducting epoxy cement has been prepared (see Hellar et al., J. Phys. Chem., 95:5970 (1991)). Cross linked redox gels for amperometric biosensors applications have also been prepared with glucose oxidase electrically connected to electrodes so that electrons were shown to flow from the enzyme, through the polymer and to the electrode (see Hellar, A., et. al., Anal. Chem., 62, 258, (1990)).

In this embodiment, it is preferred that a redox polymer such as a poly-(vinylpyridine) complex of Os(bby)$_2$Cl be cross-linked with an epoxide such as diepoxide to form a redox-conducting epoxide cement which is capable of strongly binding to electrodes made of conductive material such as gold, vitreous carbon, graphite, and other conductive materials. This strong attachment is included in the definition of "covalently attached" for the purposes of this embodiment. The epoxide cross-linking polymer is then reacted with, for example, an exposed amine, such as the amine of an amino-modified nucleic acid described above, covalently attaching the nucleic acid to the complex, forming a "redox hydrogel" on the surface of the electrode.

In an analogous fashion, chemically modified DNA can be substituted for the redox enzyme or mediator with the result of electron transfer processes being observed from a transition metal-modified DNA moiety through a coupled redox conducting polymer to an electrode.

Suitable mediators include water soluble ferrocene/ferricinium hydroquinones/quinones, reducible and oxidizable components of organic salts, cobaltocenes, the hexa- and octacyanides of molybdenum, tungsten and iron. In addition, macrocycles and chelating ligands of transition metals such as cobalt, ruthenium and nickel are used, including Co(ethylenediamine)$_3$ and Ru(ethylenediamine)$_3$ and the trisbypyridyl and hexamine complexes of transition metals such as Co, Ru, Fe, and Os (see Alyanasundaram, supra).

In a preferred embodiment, electron transport between the electrode and the nucleic acid can be direct via a covalent bond. One advantage of these systems is that the orientation of the DNA probe can be influenced to reduce any bending back of the probe onto the electrode. Also, more precise control of applied potential and measured current is associated with short covalent linkages versus gels and polymers.

In a preferred embodiment, the covalent bonds must be highly conducting such as in a redox polymer (Hellar, A. Acc. Chem. Res. Vol. 23, p. 128, 1990). Alternatively, if they are poorly conducting, the length of the linkage must be kept short. Accordingly, a preferred embodiment has an electron traversing no more than about five a bonds, with no more than three being especially preferred. Carbon paste and glassy carbon rods have proven reliable and effective as electrodes in a variety of chemical sensors, including sensitive glucose oxidase enzyme-based biosensors, and may be used in the present invention. In addition, flexible siloxane and ethylene oxide polymers covalently attached to ferrocene or Os(bpy)$_2$ molecules have been shown to be highly effective redox polymers for mediating electron transfer from several enzymes to an electrode. Amino-ribose modified nucleic acids are attached to carbon electrodes by variations of these literature techniques. Finally, nucleic acids are more directly attached to oxidized carbon electrodes via guanosine residues, using known carbodiimide and N-hydroxysuccinimide chemistry.

In a preferred embodiment, glassy carbon electrodes (GCEs) are used. In this embodiment, amine groups such as outlined above on the 2' or 3' carbon of the ribose ring are used for attachment. The reaction proceeds via the oxidation of an amine group to a cation radical which forms a chemically stable and covalent bond between the amine and the edge plane of the GCE surface (see Deinhammer, R, et al. *Langmuir* 10:1306 (1994)) This synthetic approach has been well characterized using X-ray photo-electron spectroscopy and cyclic voltammetry. The yield using this chemistry can be quite high, approximately $1 \times 10^{10}$ molecules/cm$^2$. The amine compound forms a stable bond to the carbon surface, and steric effects influence binding efficiency. The reactivity of primary amines is substantially higher than secondary amines; the binding of tertiary amines is not observed at all.

Employing the amino-modified (primary amine group) oligonucleotides described earlier, the procedure developed by Deinhammer, R, et al. to prepare the GCEs for electrochemical treatment in amine containing solution is depicted in FIG. 8A.

In addition, DNA has been immobilized onto GCEs using a water soluble carodimide (Mikkelsen et al., Electroanalysis 4:929 (1992)).

In a preferred embodiment, the nucleic acids of the invention are attached to gold electrodes. Several methods are available for the covalent attachment of redox active species to gold surfaces and electron transfer reactions with these materials have been observed. Hydroxy thiols (OH (CH$_2$)$_x$SH) of varying lengths are prepared by variation of literature procedures (see Miller, C. et al *J. Phys. Chem.* 95:877 (1991) and Chidsey, C.E.D., *Science*, V. 251, p. 919, (1991)). Example 8 outlines the preparation of hydroxyl thiols which are attached to gold electrodes.

Alternative procedures for the preparation of hydroxythiols are known in the art. Au electrodes or surfaces are prepared by literature procedures and the modified hydroxythiols adsorbed onto the Au.

In an additional embodiment, the modified nucleic acids of the invention are covalently attached to thin film oxidized surfaces. It has been reported that a variety of compounds can be covalently bonded (in the form of monolayers) to thin-film SnO$_2$, TiO$_2$, and RuO$_2$ and Pt electrodes (see Lenhard, J. and Murray, R. *J. Electroanal. Chem.* 78:195 (1977)). Reversible electrochemistry of surface bound complexes such as 3,5-dinitrobenzamide to electrodes has been observed. The reported complexes are attached to the electrode via an amide bond linkage. Employing these literature procedures, analogous derivatives using amino-modified oligonucleotides described in this work can be prepared and are schematically represented in FIG. 8B.

Accordingly, using the above methods, oligonucleotides may be attached to a solid support such that the electrode serves as either the electron donor moiety or the electron acceptor moiety.

Thus, all combinations of electron donors and acceptors may be made: two transition metal complexes; two organic electron transfer species; one transition metal, one organic moiety; one transition metal and an electrode; and one organic moiety and an electrode. The choice of the electron transfer species will depend in part on the method of initiation and detection required, as is more fully described below.

The term "target sequence" or grammatical equivalents herein means a nucleic acid sequence on a single strand of nucleic acid. The target sequence may be a portion of a gene, a regulatory sequence, genomic DNA, cDNA, mRNA, or others. It may be any length, with the understanding that longer sequences are more specific. As is outlined more fully below, probes are made to hybridize to target sequences to determine the presence or absence of the target sequence in a sample. Generally speaking, this term will be understood by those skilled in the art.

The probes of the present invention are designed to be complementary to the target sequence, such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence.

A variety of hybridization conditions may be used in the present invention. As is known in the art, "high" stringency usually refers to conditions such as 0.1×SSC at 65° C., reduced stringency conditions include 2–5×SSC at 25°–50° C. The hybridization conditions may also vary when a non-ionic backbone such as PNA is used, as is known in the art.

The terms "first target domain" and "second target domain" or grammatical equivalents herein means two portions of a target sequence within a nucleic acid which is under examination. The first target domain may be directly adjacent to the second target domain, or the first and second target domains may be separated by an intervening target domain. The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

The present invention is directed, in part, to the site-selective modification of nucleic acids with redox active moieties such as transition metal complexes for the preparation of a new series of biomaterials capable of long distance electron transfer through a nucleic acid matrix. The present invention provides for the precise placement of electron transfer donor and acceptor moieties at predetermined sites on a single stranded or double stranded nucleic acid. In general, electron transfer between electron donor and acceptor moieties in a double helical nucleic acid does not occur at an appreciable rate unless nucleotide base pairing exists in the sequence between the electron donor and acceptor in the double helical structure.

This differential in the rate of electron transfer forms the basis of a utility of the present invention for use as probes.

In the system of the present invention, where electron transfer moieties are covalently bound to the backbone of a nucleic acid, the electrons putatively travel via the π-orbitals of the stacked base pairs of the double stranded nucleic acid. The electron transfer rate is dependent on several factors, including the distance between the electron donor-acceptor pair, the free energy ($\Delta G$) of the reaction, the reorganization energy ($\lambda$), the contribution of the intervening medium, the orientation and electronic coupling of the donor and acceptor pair, and the hydrogen bonding between the bases.

The contribution of the intervening medium depends, in part, on the number of sigma ($\sigma$) bonds the electron must traverse from the electron donor to reach the bases stack, or to exit the stack to reach the electron acceptor. As is shown in FIG. 5, when the metal is bound to the ribose-phosphate backbone via an amine moiety at the 2' carbon of the ribose, an electron must travel through four $\sigma$ bonds to reach the stack: the metal to nitrogen bond, the nitrogen to 2' carbon bond, and from the 2' carbon to the base, or vice versa depending on the direction of the electron flow. Since the base of the nucleotide is conjugated in some degree, the base can be considered to be the edge of the "π-way"; that is, the conjugated π orbitals of the stacked base pairs. When the metal is bound to the ribose-phosphate backbone via the 3' carbon of the ribose, an electron must traverse through 5 $\sigma$ bonds. When the metal is bound via phosphoramide-type linkages, an electron must traverse through 7 $\sigma$ bonds. In the preferred embodiments, the compositions of the invention are designed such that the electron transfer moieties are as close to the "pi-way" as possible without significantly disturbing the secondary and tertiary structure of the double helical nucleic acid, particularly the Watson-Crick basepairing.

The effect on the electron transfer rate by the hydrogen bonding between the bases is a dependence on the actual nucleic acid sequence, since A-T pairs contain one less hydrogen bond than C-G pairs. However, this sequence dependence is overshadowed by the determination that there is a measurable difference between the rate of electron transfer within a DNA base-pair matrix, and the rate through the ribose-phosphate backbone, the solvent or other electron tunnels. This rate differential is thought to be at least several orders of magnitude, and may be as high as four orders of magnitude greater through the stacked nucleotide bases as compared to other electron transfer pathways. Thus the presence of double stranded nucleic acids, for example in gene probe assays, can be determined by comparing the rate of electron transfer for the unhybridized probe with the rate for hybridized probes.

In one embodiment, the present invention provides for novel gene probes, which are useful in molecular biology and diagnostic medicine. In this embodiment, single stranded nucleic acids having a predetermined sequence and covalently attached electron donor and electron acceptor moieties are synthesized. The sequence is selected based upon a known target sequence, such that if hybridization to a complementary target sequence occurs in the region between the electron donor and the electron acceptor, electron transfer proceeds at an appreciable and detectable rate. Thus, the present invention has broad general use, as a new form of labelled gene probe. In addition, since detectable electron transfer in unhybridized probes is not appreciable, the probes of the present invention allow detection of target sequences without the removal of unhybridized probe. Thus, the present invention is uniquely suited to automated gene probe assays or field testing.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, Salmonella, Campylobacter, *Vibrio cholerae*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

The present invention also finds use as a unique methodology for the detection of mutations in target nucleic acid sequences. As a result, if a single stranded nucleic acid containing electron transfer moieties is hybridized to a target sequence with a mutation, the resulting perturbation of the base pairing of the nucleosides will measurably affect the electron transfer rate. This is the case if the mutation is a substitution, insertion or deletion. Alternatively, two single stranded nucleic acids each with a covalently attached electron transfer species that hybridize adjacently to a target sequence may be used. Accordingly, the present invention provides for the detection of mutations in target sequences.

Thus, the present invention provides for extremely specific and sensitive probes, which may, in some embodiments, detect target sequences without removal of unhybridized probe. This will be useful in the generation of automated gene probe assays.

In an alternate embodiment double stranded nucleic acids have covalently attached electron donor and electron acceptor moieties on opposite strands. Such nucleic acids are useful to detect successful gene amplification in polymerase chain reactions (PCR), thus allowing successful PCR reactions to be an indication of the presence or absence of a target sequence. PCR may be used in this manner in several ways. For example, if one of the two PCR primers contains a 5' terminally attached electron donor, and the other contains a 5' terminally attached electron acceptor, several rounds of PCR will generate doubly labeled double stranded fragments (occasionally referred to as "amplicons"). After appropriate photoinduction, the detection of electron transfer provides an indication of the successful amplification of the target sequence as compared to when no amplification occurs. A particular advantage of the present invention is that the separation of the single stranded primers from the amplified double stranded DNA is not necessary, as outlined above for probe sequences which contain electron transfer moieties. Alternatively, the detection of a target sequence via PCR is done by attaching one electron transfer moiety species to one or both of the primers. The other electron transfer moiety species is attached to individual nucleosides of the PCR reaction pool, as is described herein. Incorporation of the nucleosides containing the electron transfer moiety into the nucleic acid during the PCR reaction results in both electron transfer species being attached either to the same single strand or to opposite strands, or both. Allowing the newly synthesized nucleic acid to remain in a hybridized form allows the detection of successful elongation via electron transfer, and thus the detection of a target sequence. In this way, the present invention is used for PCR detection of target sequences.

In another embodiment the present invention provides for double stranded nucleic acids with covalently attached electron donor and electron acceptor moieties to serve as bioconductors or "molecular wire" The electron transport may occur over distances up to and in excess of 28 Å per electron donor and acceptor pair. In addition, the rate of electron transfer is very fast, even though dependent on the distance between the electron donor and acceptor moieties. By modifying the nucleic acid in regular intervals with electron donor and/or electron acceptor moieties, it may be possible to transport electrons over long distances, thus creating bioconductors. These bioconductors are useful in a large number of applications, including traditional applications for conductors such as mediators for electrochemical reactions and processes.

In addition, these bioconductors may be useful as probes for photosynthesis reactions as well as in the construction of synthetic light harvesting systems. The current models for the electron transfer component of an artificial light harvesting system have several problems, as outlined above, including a dependence on solvent polarity and composition, and a lack of sufficient rigidity without arduous synthesis. Thus the present invention is useful as both a novel form of bioconductor as well as a novel gene probe.

The present invention provides nucleic acids with covalently attached electron transfer moieties. The electron transfer moieties may be attached to the nucleic acid at a variety of positions.

In one embodiment, the electron donor and acceptor moieties are added to the 3' and/or 5' termini of the nucleic acid on either the sugar-phosphate backbone or a terminal base. In alternative embodiments, the electron donor and acceptor moieties are added to the backbone of one or more internal nucleosides, that is, any nucleoside which is not the 3' or 5' terminal nucleoside. In a further embodiment, the electron donor and acceptor moieties are added to the backbone of both internal and terminal nucleosides.

In a preferred embodiment, the electron transfer moieties are attached to the ribose-phosphate backbone in a number of positions. As shown in FIG. 5, several positions are possible, with attachment to a ribose of the ribose-phosphate backbone being particularly preferred. Accordingly, in FIG. 5, the most preferred site of attachment of a electron transfer moiety is $M_1$, followed by $M_4$, $M_2$ and $M_3$, in that order. In a preferred embodiment, the electron transfer moieties are attached at the 2' or 3' position on the ribose, with 2' being particularly preferred.

In a preferred embodiment, the electron transfer moieties do not intercalate, and are attached such that do not intercalate. Thus, while it is possible to utilize a "linker", such as alternating double bonds to attach the electron transfer moiety to the nucleic acid, the linker is either preferably not longer than the equivalent of one or two nucleosides in length, or is not significantly flexible to allow intercalation. Preferably, if linkers are used, they are attached via the ribose of the nucleic acid backbone.

In one embodiment, the electron transfer moieties are added to the bases of the terminal nucleosides. Thus, when the target sequence to be detected is n nucleosides long, a probe can be made which has an extra terminal nucleoside at one or both of the ends of the nucleic acid (n+1 or n+2), which are used to covalently attach the electron transfer moieties but which do not participate in basepair hybridization. This extra terminal nucleoside is important since attachment of electron transfer moieties to an internal nucleoside base is expected to perturb Watson-Crick basepairing. That is, the base used for covalent attachment should be outside of the region used to identify the target sequence. Additionally, it is preferred that upon probe hybridization, the terminal nucleoside containing the electron transfer moiety covalently attached at the base be directly adjacent to Watson-Crick basepaired nucleosides; that is, the electron transfer moiety should be as close as possible to the stacked π-orbitals of the bases such that an electron travels through a minimum of σ bonds to reach the "π-way", or alternatively can otherwise electronically contact the π-way.

In one embodiment, a single stranded nucleic acid is labelled with an electron transfer moiety via the terminal bases at both ends. Alternate embodiments utilize a terminal base and a 5' or a 3' terminal ribose-phosphate attachment as described above. In further embodiments, compositions are provided comprising a first single stranded nucleic acid containing an electron donor covalently attached at a terminal base and a second single stranded nucleic acid containing an electron acceptor covalently attached at a position as described above, that is, at a 5', 3' or internal position; alternatively, the electron donor and acceptor may be switched. A particularly preferred embodiment utilizes an electrode as one of the electron transfer moieties with the other electron transfer moiety being attached to a terminal base, preferably on the same single strand.

The present invention further provides methods for the site-specific addition of electron transfer moieties to nucleic acids. As outlined above, the electron transfer moieties may be added at the 2' or 3' position of a ribose of the ribose-phosphate backbone, to a 3' or 5' terminal base, or to an internal nucleoside using peptide nucleic acid linkages, phosphoramidate bonds, phosphorothioate bonds, phosphorodithioate bonds, or O-methyl phosphoramidate bonds.

Molecular mechanics calculations indicate that perturbations due to the modification of at the ribose of the terminal nucleosides of nucleic acids are minimal, and Watson-Crick base pairing is not disrupted (unpublished data using Biograf from Molecular Simulations Inc., San Diego, Calif.).

For attachment to a ribose, a preferred embodiment utilizes modified nucleosides to attach the electron transfer moieties. Preferably amino-modified nucleosides and nucleosides are used. In an alternate embodiment, thio-modified nucleosides are used to attach the electron transfer moieties of the invention.

The modified nucleosides are then used to site-specifically add a transition metal electron transfer moiety, either to the 3' or 5' termini of the nucleic acid, or to any internal nucleoside. Either the 2' or 3' position of the ribose may be altered for attachment at the 3' terminus; for attachment to an internal ribose or the 5' terminus, the 2' position is preferred. Thus, for example, the 2' position of the ribose of the deoxyribo- or ribonucleoside is modified prior to the addition of the electron transfer species, leaving the 3' position of the ribose unmodified for subsequent chain attachment if necessary. In a preferred embodiment, an amino group is added to the 2' or 3' carbon of the sugar using established chemical techniques. (Imazawa et al., J. Org. Chem., 44:2039 (1979); Hobbs et al., J. Org. Chem. 42(4):714 (1977); Verheyden et al. J. Org. Chem. 36(2):250 (1971)).

The amino-modified nucleosides made as described above are converted to the 2' or 3' modified nucleotide triphosphate form using standard biochemical methods (Fraser et al., Proc. Natl. Acad. Sci. USA, 4:2671 (1973)).

Modified nucleosides for the attachment of the electron transfer moieties to the bases, is done as outlined in Telser, supra, both of which are expressly incorporated by reference. These modified nucleosides are then incorporated at either the 3' or 5' terminus as outlined below.

Once the modified nucleosides are prepared, protected and activated, they may be incorporated into a growing oligonucleotide by standard synthetic techniques (Gait, Oligonucleotide Synthesis: A Practical Approach, IRL Press, Oxford, UK 1984; Eckstein) in several ways. In one embodiment, one or more modified nucleosides are incorporated into a growing oligonucleotide chain by using standard molecular biology techniques such as with the use of the enzyme DNA polymerase I, T4 DNA polymerase, T7 DNA polymerase, Taq DNA polymerase, reverse transcriptase, and RNA polymerases. For the incorporation of a 3' modified nucleoside to a nucleic acid, terminal deoxynucleotidyltransferase may be used. (Ratliff, Terminal deoxynucleotidyltransferase. In The Enzymes, Vol 14A. P. D. Boyer ed. pp 105–118. Academic Press, San Diego, Calif. 1981). Alternatively, and preferably, the amino nucleoside is converted to the phosphoramidite or H-phosphonate form, which are then used in solid-phase or solution syntheses of oligonucleotides. In this way the modified nucleoside, either for attachment at the ribose (i.e. amino- or thiol-modified nucleosides) or the base, is incorporated into the oligonucleotide at either an internal position or the 5' terminus. This is generally done by protecting the 5' position of the ribose with 4',4-dimethoxytrityl (DMT) followed by reaction with 2-cyanoethoxy-bis-diisopropylaminophosphine in the presence of diisopropylammonium tetrazolide to give the phosphoramidite as is known in the art; although other techniques may be used as will be appreciated by those in the art. See Gait, supra; Caruthers, Science 230:281 (1985), both of which are expressly incorporated herein by reference.

For attachment of an electron transfer moiety to the 3' terminus, a preferred method utilizes the attachment of the modified nucleoside to controlled pore glass (CPG) or other polymeric supports. In this embodiment, the modified nucleoside is protected at the 5' end with DMT, and then reacted with succinic anhydride with activation. The resulting succinyl compound is attached to CPG or other polymeric supports as is known in the art. Further phosphoramidite nucleosides are added, either modified or not, to the 5' end after deprotection.

In other embodiments, the electron transfer moiety or moieties are added to the middle of the nucleic acid, i.e. to an internal nucleoside. This may be accomplished in three ways.

In a preferred embodiment, a modified nucleoside is incorporated at the 5' terminus as described above. In this embodiment, oligonucleotide synthesis simply extends the 5' end from the modified nucleoside using standard techniques. This results in an internally amino modified oligonucleotide.

In one embodiment, the nucleosides are modified to contain an aromatic amine capable of binding an electron transfer moiety at either the 2' or 3' position of the ribose. For example, one of the nitrogens of imidazole can be attached at the 2' or 3' position of the ribose and thus used to attach the electron transfer moiety such as a transition metal complex. This may effectively reduce the number of σ bonds an electron must travel through to reach the "pi-way" since the imidazole offers substantially less resistance to electron transfer as compared to a σ bond. In a preferred embodiment, the imidazole is attached at the 2' position of the ribose. In an alternate embodiment, the imidazole is attached at the 3' position. The imidazole-modified nucleoside may be incorporated into an oligonucleotide as outlined herein for amino-modified nucleosides.

In an alternate embodiment, electron transfer moieties are added to the backbone at a site other than ribose, resulting in an internal attachment. For example, phosphoramide rather than phosphodiester linkages can be used as the site for transition metal modification. These transition metals serve as the donors and acceptors for electron transfer reactions. While structural deviations from native phosphodiester linkages do occur and have been studied using CD and NMR (Heller, Acc. Chem. Res. 23:128 (1990); Schuhmann et al. J. Am. Chem. Soc. 113:1394 (1991)), the phosphoramidite internucleotide link has been reported to bind to complementary polynucleotides and is stable (Beaucage et al., supra, and references therein; Letsinger, supra; Sawai, supra; Jager, Biochemistry 27:7237 (1988)). In this embodiment, dimers of nucleotides are created with phosphoramide linkages at either the 2'-5' or 3'-5' positions. A preferred embodiment utilizes the 3'-5' position for the phosphoramide linkage, such that structural disruption of the subsequent Watson-Crick basepairing is minimized. These dimer units are incorporated into a growing oligonucleotide chain, as above, at defined intervals, as outlined below.

Thus, the present invention provides methods for making a nucleic acid with covalently attached electron transfer moieties. In a preferred embodiment, the method is for making a nucleic acid with an electron transfer moiety attached at the 3' terminus of said nucleic acid. The method comprises attaching a 2'-amino modified nucleoside to control pore glass, and adding phosphoramidite nucleosides to the 5' terminus of the modified nucleoside to form a nucleic acid. The nucleic acid is then optionally cleaved from the CPG using known methods. The nucleic acid may be hybridized to its complement, to protect the bases from modification, if required, and the electron transfer moiety is added to the 2'-amino modified nucleoside.

In a preferred embodiment, methods for making a nucleic acid with an electron transfer moiety attached at the 5' terminus are provided. The method comprises attaching a nucleoside to control pore glass, and adding phosphoramidite nucleosides to the 5' terminus of the nucleoside to form a nucleic acid. A 2' or 3' amino modified nucleoside is added to the 5' terminus, and the nucleic acid is optionally cleaved from the CPG. The nucleic acid may be hybridized to its complement if required, and the electron transfer moiety is added to the 2' or 3'-amino modified nucleoside.

In a preferred embodiment, a method for making a single stranded nucleic acid with electron transfer moieties attached at both the 3' and 5' terminus. The method comprises attaching a modified nucleoside to control pore glass. The modified nucleoside may be either amino-modified, for attachment via the ribose as described herein, or modified at the base. Additional phosphoramidite nucleosides are added to the 5' terminus of the modified nucleoside to form a nucleic acid. A modified phosphoramidite nucleoside is further added to the 5' terminus of the nucleic acid, which is then optionally cleaved off the control pore glass and may be hybridized to its complement. An electron donor moiety is added to one modified nucleoside and an electron acceptor moiety is added to the other modified nucleoside.

The cleavage from the CPG may occur either prior to transition metal modification or afterwards.

It should be understood that it is important that the basepairing of the nucleoside bases is not significantly perturbed in order to allow hybridization, good electron transfer rates, and the detection of mismatches. Thus, for example, the transition metal moieities, when attached to the nucleic acids of the invention, do not intercalate, i.e. insert and stack between the basepairs of the double stranded nucleic acid. Intercalation of the transition metals with the accompanying ligands disturbs the basepairing, and thus hinders the transfer of electrons and the identification of mismatches. Similarly, with the exception of terminal bases, as is outlined below, attaching the transition metal complexes at the nucleoside bases (Telser et al., supra) also disturbs the basepairing and impedes the identification of mismatches.

It should be noted that when using the above techniques for the modification of internal residues it is possible to create a nucleic acid that has an electron transfer species on the next-to-last 3' terminal nucleoside, thus eliminating the need for the extra steps required to produce the 3' terminally labelled nucleoside.

In a further embodiment for the modification of internal residues, 2' or 3' modified nucleoside triphosphates are generated using the techniques described above for the 3' nucleoside modification. The modified nucleosides are inserted internally into nucleic acid using standard molecular biological techniques for labelling DNA and RNA. Enzymes used for said labelling include DNA polymerases such as polymerase I, T4 DNA polymerase, T7 DNA polymerase, Taq DNA polymerase, reverse transcriptase and RNA polymerases such as E. coli RNA polymerase or the RNA polymerases from phages SP6, T7 or T3 (Short Protocols in Molecular Biology, 1992. Ausubel et al. Ed. pp 3.11–3.30).

As described above, the electron transfer moiety, preferably a transition metal complex, may be attached to any of the five bases (adenine, thymine, uracil, cytosine, guanine and other non-naturally occurring bases such as inosine, xanthine, and hypoxanthine, among others). This is done using well known techniques; see Telser et al., J. Am. Chem. Soc. 111:7226–7232 (1989); Telser et al., J. Am. Chem. Soc. 111:7221–7226 (1989). As outlined herein, these terminally modified nucleosides may be attached to the nucleic acid enzymatically as is known in the art, using DNA polymerases; alternatively, the modified nucleosides may be incorporated into a growing oligonucleotide chain using traditional phosphoramidite chemistry during oligonucleotide synthesis as is outlined herein.

The exposed amine or other ligand at the 2' or 3' position of the ribose, the phosphoramide linkages, or the other linkages useful in the present invention, are readily modified with a variety of electron transfer moieties, and particularly transition metal complexes with techniques readily known in the art (see for example Millet et al, in Metals in Biological Systems, Sigel et al. Ed. Vol. 27, pp 223–264, Marcell Dekker Inc. New York, 1991 and Durham, et al. in ACS Advances in Chemistry Series, Johnson et al. Eds., Vol. 226, pp 180–193, American Chemical Society, Washington D.C.; and Meade et al., J. Am. Chem. Soc. 111:4353 (1989)). Generally, these techniques involve contacting a partially chelated transition metal complex with the amine group of the modified nucleoside.

The organic electron transfer species are also added to the functional group of the modified nucleoside such as an amine group, using techniques known in the art.

When peptide nucleic acids (PNA) are used, attachment of the electron transfer moieties proceeds as follows. The amino group at the N-terminus of the PNA will bind a partially chelated transition metal or organic electron transfer moiety similar to the amino-modified ribose. Addition to the carboxy terminus can proceed in a variety of ways, one of which is depicted in FIG. 7. Additionally, for single stranded PNAs, one electron transfer moiety may be attached to the N-terminus, and the other electron transfer moiety is attached to the terminal base at the carboxy terminus. Alternatively, both transfer moieties are attached to terminal bases. Similar combinations may be made for two single stranded nucleic acids, each containing an electron transfer moiety.

In addition, the present invention provides a novel method for the site specific addition to the ribose-phosphate backbone of a nucleic acid of electron donor and electron acceptor moieties to a previously modified nucleoside.

In one embodiment, the electron donor and acceptor moieties are attached to the modified nucleoside by methods which utilize a unique protective hybridization step. In this embodiment, the modified single strand nucleic acid is hybridized to an unmodified complementary sequence. This blocks the sites on the heterocyclic bases that are susceptible to attack by the transition metal electron transfer species.

When the terminal bases are to be labelled with electron transfer species, the complementary sequence does not extend to the base to be labelled. That is, a complementary sequence of n nucleosides in length is chosen for hybridization to a probe sequence of n+1 or n+2, such that the terminal base is not protected. Thus the unprotected base is exposed to the electron transfer moiety such that the moiety is attached to the base.

After successful addition of the desired metal complex, the modified duplex nucleic acid is separated into single strands using techniques well known in the art.

In a preferred embodiment, single stranded nucleic acids are made which contain one electron donor moiety and one electron acceptor moiety. The electron donor and electron acceptor moieties may be attached at either the 5' or 3' end of the single stranded nucleic acid. Alternatively, the electron transfer moieties may be attached to internal nucleosides, or one to an internal nucleoside and one to a terminal nucleoside. It should be understood that the orientation of the electron transfer species with respect to the 5'-3' orientation of the nucleic acid is not determinative. Thus, as outlined in FIG. 1, any combination of internal and terminal nucleosides may be utilized in this embodiment.

In an alternate preferred embodiment, single stranded nucleic acids with at least one electron donor moiety and at least one electron acceptor moiety are used to detect mutations in a complementary target sequence. A mutation, whether it be a substitution, insertion or deletion of a nucleoside or nucleosides, results in incorrect base pairing in a hybridized double helix of nucleic acid. Accordingly, if the path of an electron from an electron donor moiety to an electron acceptor moiety spans the region where the mismatch lies, the electron transfer will be eliminated or reduced such that a change in the relative rate will be seen. Therefore, in this embodiment, the electron donor moiety is attached to the nucleic acid at a 5' position from the mutation, and the electron acceptor moiety is attached at a 3' position, or vice versa.

In this embodiment it is also possible to use an additional label on the modified single stranded nucleic acid to detect hybridization where there is one or more mismatches. If the complementary target nucleic acid contains a mutation, electron transfer is reduced or eliminated. To act as a control, the modified single stranded nucleic acid may be radio- or fluorescently labeled, such that hybridization to the target sequence may be detected, according to traditional molecular biology techniques. This allows for the determination that the target sequence exists but contains a substitution, insertion or deletion of one or more nucleosides. Alternatively, single stranded nucleic acids with at least one electron donor moiety and one electron acceptor moiety which hybridize to regions with exact matches can be used as a controls for the presence of the target sequence.

It is to be understood that the rate of electron transfer through a double stranded nucleic acid helix depends on the nucleoside distance between the electron donor and acceptor moieties. Longer distances will have slower rates, and consideration of the rates will be a parameter in the design of probes and bioconductors. Thus, while it is possible to measure rates for distances in excess of 100 nucleosides, a preferred embodiment has the electron donor moiety and the electron acceptor moiety separated by at least 3 and no more than 100 nucleosides. More preferably the moieties are separated by 8 to 64 nucleosides, with 15 being the most preferred distance.

In addition, it should be noted that certain distances may allow the utilization of different detection systems. For example, the sensitivity of some detection systems may allow the detection of extremely fast rates; i.e. the electron transfer moieties may be very close together. Other detection systems may require slightly slower rates, and thus allow the electron transfer moieties to be farther apart.

In an alternate embodiment, a single stranded nucleic acid is modified with more than one electron donor or acceptor moiety. For example, to increase the signal obtained from these probes, or decrease the required detector sensitivity, multiple sets of electron donor-acceptor pairs may be used.

As outlined above, in some embodiments different electron transfer moieties are added to a single stranded nucleic acid. For example, when an electron donor moiety and an electron acceptor moiety are to be added, or several different electron donors and electron acceptors, the synthesis of the single stranded nucleic acid proceeds in several steps. First partial nucleic acid sequences are made, each containing a single electron transfer species, i.e. either a single transfer moiety or several of the same transfer moieties, using the techniques outlined above. Then these partial nucleic acid sequences are ligated together using techniques common in the art, such as hybridization of the individual modified partial nucleic acids to a complementary single strand, followed by ligation with a commercially available ligase.

Alternatively, single stranded nucleic acid may be made by incorporating an amino modified nucleoside at two positions using the above techniques. As a result of the synthesis, one of the amino modified nucleosides has a temporary protecting group on the amine such as DMT. Upon hybridization to the complementary unmodified strand, the unprotected amine is exposed to the first electron transfer moiety, i.e. either a donor or an acceptor, resulting in covalent attachment. The protecting group of the protected amino-modified nucleoside is then removed, and the hybrid is contacted with the second electron transfer species, and the strands separated, resulting in a single strand being labelled with both a donor and acceptor. The single strand containing the proper electron transfer moieties is then purified using traditional techniques.

In a preferred embodiment, single stranded nucleic acids are made which contain one electron donor moiety or one electron acceptor moiety. The electron donor and electron acceptor moieties are attached at either the 5' or 3' end of the single stranded nucleic acid. Alternatively, the electron transfer moiety is attached to an internal nucleoside.

It is to be understood that different species of electron donor and acceptor moieties may be attached to a single stranded nucleic acid. Thus, more than one type of electron donor moiety or electron acceptor moiety may be added to any single stranded nucleic acid.

In a preferred embodiment, a first single stranded nucleic acid is made with on or more electron donor moieties attached. A second single stranded nucleic acid has one or more electron acceptor moieties attached. In this embodiment, the single stranded nucleic acids are made for use as probes for a complementary target sequence. In one embodiment, the complementary target sequence is made up of a first target domain and a second target domain, where the first and second sequences are directly adjacent to one another. In this embodiment, the first modified single stranded nucleic acid, which contains only electron donor moieties or electron acceptor moieties but not both, hybridizes to the first target domain, and the second modified single stranded nucleic acid, which contains only the corresponding electron transfer species, binds to the second target domain. The relative orientation of the electron transfer species is not important, as outlined in FIG. 2, and the present invention is intended to include all possible orientations.

In the design of probes comprised of two single stranded nucleic acids which hybridize to adjacent first and second target sequences, several factors should be considered. These factors include the distance between the electron donor moiety and the electron acceptor moiety in the hybridized form, and the length of the individual single stranded probes. For example, it may be desirable to synthesize only 5' terminally labelled probes. In this case, the single stranded nucleic acid which hybridizes to the first sequence may be relatively short, such that the desirable distance between the probes may be accomplished. For example, if the optimal distance between the electron transfer moieties is 15 nucleosides, then the first probe may be 15 nucleosides long.

In one aspect of this embodiment, the two single stranded nucleic acids which have hybridized to the adjacent first and second target domains are ligated together prior to the electron transfer reaction. This may be done using standard molecular biology techniques utilizing a DNA ligase, such as T4 DNA ligase.

In an alternative embodiment, the complementary target sequence will have a first target domain, an intervening target domain, and a second target domain. In this embodiment, the first modified single stranded nucleic acid, which contains only electron donor moieties or electron acceptor moieties but not both, hybridizes to the first target domain, and the second modified single stranded nucleic acid, which contains only the corresponding electron transfer species, binds to the second target domain. When an intervening single stranded nucleic acid hybridizes to the intervening target sequence, electron transfer between the donor and acceptor is possible. The intervening sequence may be any length, and may comprise a single nucleoside. Its length, however, should take into consideration the desirable distances between the electron donor and acceptor moieties on the first and second modified nucleic acids. Intervening sequences of lengths greater than 14 are desirable, since the intervening sequence is more likely to remain hybridized to form a double stranded nucleic acid if longer intervening sequences are used. The presence or absence of an intervening sequence can be used to detect insertions and deletions.

In one aspect of this embodiment, the first single stranded nucleic acid hybridized to the first target domain, the intervening nucleic acid hybridized to the intervening domain, and the second single stranded nucleic acid hybridized to the second target domain, may be ligated together prior to the electron transfer reaction. This may be done using standard molecular biology techniques. For example, when the nucleic acids are DNA, a DNA ligase, such as T4 DNA ligase can be used.

The complementary target single stranded nucleic acid of the present invention may take many forms. For example, the complementary target single stranded nucleic acid sequence may be contained within a larger nucleic acid sequence, i.e. all or part of a gene or mRNA, a restriction fragment of a plasmid or genomic DNA, among others. One skilled in the art of molecular biology would understand how to construct useful probes for a variety of target sequences using the present invention.

In one embodiment, two single stranded nucleic acids with covalently attached electron transfer moieties have complementary sequences, such that they can hybridize together to form a bioconductor. In this embodiment, the hybridized duplex is capable of transferring at least one electron from the electron donor moiety to the electron acceptor moiety. In a preferred embodiment, the individual single stranded nucleic acids are aligned such that they have blunt ends; in alternative embodiments, the nucleic acids are aligned such that the double helix has cohesive ends. In either embodiment, it is preferred that there be uninterrupted double helix base-pairing between the electron donor moiety and the electron acceptor moiety, such that electrons may travel through the stacked base pairs.

In one bioconductor embodiment, the double stranded nucleic acid has one single strand nucleic acid which carries all of the electron transfer moieties.

In another embodiment, the electron transfer moieties may be carried on either strand, and in any orientation. For example, one strand may carry only electron donors, and the other only electron acceptors or both strands may carry both.

In one embodiment, the double stranded nucleic acid may have different electron transfer moieties covalently attached in a fixed orientation, to facilitate the long range transfer of electrons. This type of system takes advantage of the fact that electron transfer species may act as both electron donors and acceptors depending on their oxidative state. Thus, an electron donor moiety, after the loss of an electron, may act as an electron acceptor, and vice versa. Thus, electron transfer moieties may be sequentially oriented on either strand of the double stranded nucleic acid such that directional transfer of an electron over very long distances may be accomplished. For example, a double stranded nucleic acid could contain a single electron donor moiety at one end and electron acceptor moieties, of the same or different composition, throughout the molecule. A cascade effect of electron transfer could be accomplished in this manner, which may result in extremely long range transfer of electrons. This may be accomplished, for example, by incorporating transition metal complexes that possess a range in oxidation potentials due to ligand substitutions made at the metal center.

The choice of the specific electron donor and acceptor pairs will be influenced by the type of electron transfer measurement used; for a review, see Winkler et al., Chem. Rev. 92:369–379 (1992). When a long-lived excited state can be prepared on one of the redox sites, direct measurement of the electron transfer rate after photoinduction can be measured, using for example the flash-quench method of Chang et al., J. Amer. Chem. Soc. 113:7057 (1991). In this preferred embodiment, the excited redox site, being both a better acceptor and donor than the ground-state species, can transfer electrons to or from the redox partner. An advantage of this method is that two electron transfer rates may be measured: the photoinduced electron transfer rates and thermal electron-hole recombination reactions. Thus differential rates may be measured for hybridized nucleic acids with perfect complementarity and nucleic acids with mismatches.

In alternative embodiments, neither redox site has a long lived excited state, and electron transfer measurements depend upon bimolecular generation of a kinetic intermediate. For a review, see Winkler et al., supra. This intermediate then relaxes to the thermodynamic product via intramolecular electron transfer using a quencher, as seen below:

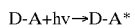
D-A+hv→D-A*

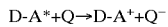
D-A*+Q→D-A⁺+Q⁻

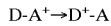
D-A⁺→D⁺-A

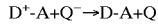
D⁺-A+Q⁻→D-A+Q

The upper limit of measurable intramolecular electron transfer rates using this method is about $10^4$ per second.

Alternative embodiments use the pulse-radiolytic generation of reducing or oxidizing radicals, which inject electrons into a donor or remove electrons from a donor, as reviewed in Winkler et al., supra.

As is appreciated in the art, there are a variety of ways to initiate and detect the electron transfer.

Electon transfer can be initiated and detected using a wide variety of methods, including, but not limited to, electrical, electrochemical, electromagnetic radiation (optical) and chemical methods. It is possible to make a variety of compositions utilizing different electron transfer moieties depending on the desired methods of initiating electron transfer and detection of electron transfer. Table 2 depicts a variety of preferred combinations for initiation and detection of electron transfer in the complexes of the invention.

TABLE 2

| Initiation | Detection | Description |
|---|---|---|
| light | light | absorbance, fluorescence, phosphorescence, refractive index, surface plasmon resonance, electron spin resonance |
| light | current | amperommetry, voltammetry, capacitance, impedance, opto-electonic detection, photo- |

TABLE 2-continued

| Initiation | Detection | Description |
|---|---|---|
| | | amperometry |
| light plus electronic initiation | light | absorbance, fluorescence, phosphorescence, refractive index, surface plasmon resonance, electron spin resonance |
| light plus electronic initiation | current | amperommetry, voltammetry, capacitance, impedance, opto-electonic detection, photo-amperommetry, amperommetric detection, cyclic voltammetry |
| electronic initiation | current | amperommetry, voltammetry, capacitance, impedance, amperommetric detection, cyclic voltammetry |
| electronic initiation | light | chemiluminescence, electrochemiluminescence, electroluminescence |

By "light" herein is meant electromagnetic radiation, with light in the UV, visible and infrared range being preferred, and UV and visible being the most preferred.

In a preferred embodiment, initiation of electron transfer is via direct or indirect photoactivation ("light in"). Simply, electromagnetic radiation of appropriate wavelength strikes the redox molecule on one end of the DNA causing excitation of a donor moiety electron which either decays immediately or is involved in intramolecular electron transfer. The efficiency with which electron transfer is induced depends upon the electronic coupling between the electron donor and acceptor and therefore depends on whether the nucleic acid is single or double stranded. In addition, the efficiency of electron transfer depends upon the extinction coefficient of the electron donor at the wavelength of light used (higher is better) and upon the lifetime of the donor electron excited state (longer is better). Preferred donor complexes therefore include acridine orange, N,N'-dimethyl-2,7-diazapyrenium dichloride ($DAP^{2+}$), methylviologen, ethidium bromide, quinones such as N,N'-dimethylanthra(2,1,9-def.6,5,10-d'e'f')diisoquinoline dichloride ($ADIQ^{2+}$); porphyrins ([meso-tetrakis(N-methyl-x-pyridinium)porphyrin tetrachloride]. Transition metal donors and acceptors include complexes of ruthenium, rhenium and osmium (most preferred) where at least one of the ligands is a chromophore.

Photoactivation can also be used to excite "mediators" that transfer energy to the electron donor moiety on the DNA via an inter-molecular process. Such mediators include water soluble and stable complexes of the transition metals, including molybdenum and tungsten halides, trisbipyridyl complexes of rhenium, osmium and ruthenium. In addition, other examples include bipyridyl and pyridyl complexes such as $Re(bpy)(CO)_3X$ where X is a halide and $Re(py)_4O_2$. Other examples include transition metal dimers such as $[Re_2Cl_8]^{2-}$ and $[Pt_2(P_2O_5H_2)_4]^{4-}$. Ruthenium trisbypyridine ($Ru^{2+}(bpy)_3$) is most preferred.

In the preferred embodiment, electron transfer occurs after photoinduction with a laser. In this embodiment, electron donor moieties may, after donating an electron, serve as electron acceptors under certain circumstances. Similarly, electron acceptor moieties may serve as electron donors under certain circumstances.

A preferred embodiment utilizes electronic activation, with voltage being preferred. A potential is applied to a sample containing modified nucleic acid probes either via a direct linkage of the modified nucleic acid to an electrode, or using electron transport mediators. Direct linkage can involve a redox active polymer to shuttle electrons from (and to, if the electrode is also used for detection) the electrode. Such polymers are outlined below. Alternatively, the direct connection can involve a relatively poorly conducting linkage provided the linkage is kept reasonably short (less than six sigma bonds). Preferred linkages will be three or fewer sigma bonds in length to allow efficient transfer of electrons from the electrode, as is outlined below.

Indirect electron transfer initiation involves electron transfer mediators or effective diffusional electron donors and acceptors such as water soluble ferrocene/ferricinium, hydroquinones/quinones, reducible and oxidizable components of organic salts, cobaltocenes, the hexa- and octacyanides of molybdenum, tungsten and iron. In addition, other examples include macrocycles and chelating ligands of transition metals such as cobalt, ruthenium and nickel, including Co(ethylenediamine)$_3$ and Ru(ethylenediamine)$_3$ and the trisbypyridyl and hexamine complexes of transition metals such as Co, Ru, Fe, and Os. See K. Alyanasundaram, Coord. Chem. Rev. V.46, p. 159, 1982. Finally, organic molecules such as 4,4'-bipyridine and 4-mercaptopyridine are examples where ferrocene is most preferred.

Precise control and variations in the applied potential can be via a potentiostat and a three electrode system (one reference, one sample and one counter electrode). This allows matching of applied potential to peak electron transfer potential of the system which depends in part on the choice of electron acceptors attached to the nucleic acid. High driving forces are achieved using bisbipyridyl complexes of transition metals, for example, ruthenium and rhenium bisbipyridyl complexes such as (Ru(bpy)$_2$im-) as electron acceptors.

Alternatively, electrochemical initiation of electron transfer may be used. The redox states of the electron donating and accepting moieties attached to nucleic acid can be electrochemicaly changed using water soluble chemical oxidants and reductants, either with or without photo- or electrical activation. Such compounds include numerous derivatives known in the art (T. Kuwana, Electrochemical Studies of Biological Systems, (D. T. Sawyer Ed.) ACS Symp. Series #38, (1977)) and include hexacyano iron complexes, zinc-mercury amalgam, and trisphenanthroline complexes of ruthenium and iron.

Electron transfer through nucleic acid can be detected in a variety of ways. A variety of detection methods may be used, including, but not limited to, optical detection, which includes fluorescence, phosphorescence, and refractive index; and electronic detection, including, but not limited to, amperommetry, voltammetry, capacitance and impedence. These methods include time or frequency dependent methods based on AC or DC currents, pulsed methods, lock-in techniques, filtering (high pass, low pass, band pass), and time-resolved techniques including time-resolved fluorescence. In some embodiments, all that is required is electron transfer detection; in others, the rate of electron transfer may be determined.

In one embodiment, the efficient transfer of electrons from one end of a nucleic acid double helix to the other results in stereotyped changes in the redox state of both the electron donor and acceptor. With many electron transfer moieties including the complexes of ruthenium containing bipyridine, pyridine and imidazole rings, these changes in redox state are associated with changes in spectral properties ("light out"). Significant differences in absorbance are observed between reduced and oxidized states for these molecules. These differences can be monitored using a spectrophotometer or simple photomultiplier tube device.

In this embodiment, possible electron donors and acceptors include all the derivatives listed above for photoactivation or initiation. Preferred electron donors and acceptors have characteristically large spectral changes upon oxidation and reduction (large extinction coefficient "deltas") resulting in highly sensitive monitoring of electron transfer. Such examples include Ru(NH$_3$)$_4$py and Ru(bpy)$_2$im as preferred examples. It should be understood that only the donor or acceptor that is being monitored by absorbance need have ideal spectral characteristics. That is, the electron acceptor can be optically invisible if only the electron donor is monitored for absorbance changes.

In a preferred embodiment, the electron transfer is detected fluorometrically. Numerous transition metal complexes, including those of ruthenium, have distinct fluorescence properties. Therefore, the change in redox state of the electron donors and electron acceptors attached to the nucleic acid can be monitored very sensitively using fluorescence. Highly efficient electron transfer through double stranded nucleic acid can, for example, result in the production of fluorescent Ru(4,7-biphenyl$_2$-phenanthroline)$_3^{2+}$ at one end of a nucleic acid probe when the electron transfer moiety on the other end is excited. The production of this compound can be easily measured using standard fluorescence assay techniques. For example, laser induced fluorescence can be recorded in a standard single cell fluorimeter, a flow through "on-line" fluorimeter (such as those attached to a chromatography system) or a multi-sample "plate-reader" similar to those marketed for 96-well immuno assays.

Alternatively, fluorescence can be measured using fiber optic sensors with nucleic acid probes in solution or attached to the fiber optic. Fluorescence is monitored using a photomultiplier tube or other light detection instrument attached to the fiber optic. The advantage of this system is the extremely small volumes of sample that can be assayed.

In addition, scanning fluorescence detectors such as the Fluorimager sold by Molecular Dynamics are ideally suited to monitoring the fluorescence of modified nucleic acid molecules arrayed on solid surfaces. The advantage of this system is the large number of electron transfer probes that can be scanned at once using chips covered with thousands of distinct nucleic acid probes.

Many transition metal complexes display fluorescence with large Stokes shifts. Suitable examples include bis- and trisphenanthroline complexes and bis- and trisbipyridyl complexes of transition metals such as ruthenium (see Juris, A., Balzani, V., et. al. Coord. Chem. Rev., V. 84, p. 85–277, 1988). Preferred examples display efficient fluorescence (reasonably high quantum yields) as well as low reorganization energies. These include Ru(4,7-biphenyl$_2$-phenanthroline)$_3^{2+}$ and Ru(4,4'-diphenyl-2,2'-bipyridine)$_3^{2+}$.

Alternatively, a reduction in fluorescence associated with hybridization can be measured using these systems. An electron transfer "donor" molecule that fluoresces readily when on single stranded nucleic acid (with an "acceptor" on the other end) will undergo a reduction in fluorescent intensity when complementary nucleic acid binds the probe allowing efficient transfer of the excited state electron. This drop in fluorescence can be easily monitored as an indicator of the presence of a target sequence using the same methods as those above.

In a further embodiment, electrochemiluminescence is used as the basis of the electron transfer detection. With some electron transfer moieties such as Ru$^{2+}$(bpy)$_3$, direct luminescence accompanies excited state decay. Changes in this property are associated with nucleic acid hybridization and can be monitored with a simple photomultiplier tube arrangement (see Blackburn, G. F. *Clin. Chem.* 37:1534–1539 (1991); and Juris et al., supra.

In a preferred embodiment, electronic detection is used, including amperommetry, voltammetry, capacitance, and impedence. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; and photoelectrochemistry.

In a preferred embodiment, monitoring electron transfer through nucleic acid is via amperometric detection, either directly using a covalently attached electrode, or indirectly using electron transport "mediators" to shuttle electrons from the nucleic acid to an electrode. Modes of attaching nucleic acids to electrodes and possible mediators are described below. An amperometric detector would resemble the numerous enzyme-based biosensors currently used to monitor blood glucose, for example. This method of detection involves applying a potential (as compared to a separate reference electrode) between the nucleic acid-conjugated electrode and an auxiliary (counter) electrode in the sample containing target genes of interest. Electron transfer of differing efficiencies is induced in samples in the presence or absence of target nucleic acid; that is, the single stranded probe exhibits a different rate than the probe hybridized to the target sequence. The differing efficiencies of electron transfer result in differing currents being generated in the electrode.

The device for measuring electron transfer amperometrically involves sensitive (nanoamp to picoamp) current detection and includes a means of controlling the voltage potential, usually a potentiostat. This voltage is optimized with reference to the potential of the electron donating complex on the nucleic acid. Possible electron donating complexes include those previously mentioned with complexes of ruthenium being preferred and complexes of rhenium being most preferred.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer through nucleic acid. In addition, other properties of insulators (such as resistance) and of conductors (such as conductivity, impedance and capicitance) could be used to monitor electron transfer through nucleic acid. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal-to-noise results of monitors based on absorbance, fluorescence and electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, between two and four orders of magnitude improvements in signal-to-noise may be achieved.

In a preferred embodiment, DNA is modified by the addition of electron donor and electron acceptor moieties. In an alternative embodiment, RNA is modified. In a further embodiment, a double stranded nucleic acid for use as a bioconductor will contain some deoxyribose nucleosides, some ribose nucleosides, and a mixture of adenosine, thymidine, cytosine, guanine and uracil bases.

In accordance with a further aspect of the invention, the preferred formulations for donors and acceptors will possess a transition metal covalently attached to a series of ligands and further covalently attached to an amine group as part of the ribose ring (2' or 3' position) or to a nitrogen or sulfur atom as part of a nucleoside dimer linked by a peptide bond, phosphoramidate bond, phosphorothioate bond, phosphorodithioate bond or O-methyl phosphoramidate bond.

In a preferred embodiment, an oligonucleotide containing at least one electron transfer moiety is attached to an electrode, which also serves as an electron transfer moiety, thus forming a single stranded nucleic acid with both an electron donor moiety and an electron acceptor moiety attached in the manner outlined above. Preferably, the single stranded nucleic acid containing an electron transfer moiety is attached covalently or in such a way that allows the transfer of electrons from the electrode to the single stranded nucleic acid in order to allow electron transfer between the electron donor and acceptor. Preferably, the non-electrode electron transfer moiety is attached at or near the terminus of the oligonucleotide, such that the probe sequence to be hybridized to the target sequence is between the donor and acceptor. The electrode may be immersed in a sample containing the target sequence such that the target sequence hybridizes to the probe and electron transfer may be detected using the techniques outlined above.

In an additional embodiment, two nucleic acids are utilized as probes as described previously. For example, one nucleic acid is covalently attached to a solid electrode which serves as an electron transfer moiety, and the other, with a covalently attached electron transfer moiety, is free in solution. Upon hybridization of a target sequence, the two nucleic acids are aligned such that electron transfer between the electron transfer moiety of the hybridized nucleic acid and the electrode occurs. The electron transfer is detected as outlined above, using techniques well known in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. The references cited herein are expressly incorporated by reference.

EXAMPLES

The amino-modified monomer units are prepared by variation of published procedures and are incorporated into a growing oligonucleotide by standard synthetic techniques. The procedure is applicable to both DNA and RNA derivatives.

Example 1

Synthesis of an Oligonucleotide Duplex with Electron Transfer Moieties at the 5' Termini In this example an eight nucleotide double stranded nucleic acid was produced, with each single strand having a single electron transfer moiety covalently attached to the 5' terminal uridine nucleotide at the 2' carbon of the ribose sugar.

Step 1: Synthesis of 5'-di(p-methoxyphenyl)methyl ether-2'-(trifluoroacetamido)-2'-deoxyuridine 2'-(trifluoroacetamido)-2'-deoxyuridine (2.0 g, 5.9 mmoles) prepared by minor modification of published procedures (Imazawa, supra) was repeatedly dissolved in a minimum of very dry $CH_3CN$ and rotary evaporated to dryness and then transferred to inert atmosphere vacuum line and further dried for a period of 1 hour. The following procedure for the synthesis of the material was adapted from Gait (supra): Under positive pressure argon, the material was dissolved in freshly dried and distilled pyridine and with stirring, 0.05 equivalents (wt.) of 4-dimethylaminopyridine (DMAP), 1.5 equivalents of triethylamine (TEA) and 1.2 equivalents of 4,4'-dimethoxytrityl chloride (DMTr-Cl) were added to the reaction mixture. The progress of the reaction was monitored by silica gel TLC (98:2 methylene chloride:methanol, mobile phase). After 30 minutes, an additional 0.5 equivalents each of DMTr-Cl and TEA were added and the reaction allowed to proceed for an additional three hours. To this reaction mixture was added an equal volume of water and the solution extracted several times with diethyl ether. The ether layers were rotary evaporated to dryness, redissolved in a minimum amount of methylene chloride and purified by flash chromatography (99:1 methylene chloride:methanol, mobile phase), to obtain the 5'-di(p-methoxyphenyl)methyl ether-2'-(trifluoroacetamido)-2'-deoxyuridine product.

Step 2: 5'-2'-aminouridine-GCTACGA and 5'-2'-aminouridine-CGTAGCA

5'-di(p-methoxyphenyl)methyl ether-2'-(trifluoroacetamido)-2'-deoxyuridine was dried under reduced pressure (glass) and dissolved in freshly dried and distilled $CH_3CN$ and placed in a specially made conical vial and placed on an ABI DNA synthesizer. The program for the preparation of standard (i.e. unmodified) oligonucleotides was altered during the final base (amino-modified) addition to a 15–30 minute coupling time. The oligonucleotide was cleaved from the column by standard procedures and purified by C-18 reverse phase HPLC. In this manner 5'-2'-aminouridine-GCTACGA and 5'-2'-aminouridine-CGTAGCA were prepared. In addition, unmodified complementary strands to both products were made for use in the electron transfer moiety synthesis below.

Step 3: 5'-2'-ruthenium bisbipyridineimidazole-aminouridine-GCTACGA

5'-2'-aminouridine GCTACGA produced in the previous step was annealed to the complementary unmodified strand using standard techniques. All manipulations of the annealed duplex, prior to the addition of the transition metal complex were handled at 4° C. In order to insure that the DNA remained annealed during modification, the reactions were performed in 1M salt. The 5'-amino modified duplex DNA was dissolved in 0.2M HEPES, 0.8M NaCl, pH 6.8 and repeatedly evacuated on a Schlenk line. Previously prepared ruthenium bisbipyridine carbonate was dissolved in the above buffer and oxygen was removed by repeated evacuation and purging with argon via a Schlenk line. The ruthenium complex was transferred to the DNA solution via cannulation (argon/vacuum) and the reaction allowed to proceed under positive pressure argon with stirring for 24 hours. To this reaction, 50 equivalents of imidazole was added to the flask and the reaction allowed to proceed for an additional 24 hours. The reaction mixture was removed from the vacuum line and applied to a PD-10 gel filtration column and eluted with water to remove excess ruthenium complex. The volume of the collected fractions was reduced to dryness via a speed vac and the solid taken up in 0.1M triethylammonium acetate (TEAC) pH 6.0. The duplex DNA was heated to 60° C. for 15 minutes with 50% formamide to denature the duplex. The single stranded DNA was purified using a C-18 reverse phase HPLC column equiped with a diode array detector and employing a gradient from 3% to 35% acetonitrile in 0.1M TEAC, pH 6.0.

Step 4: 5'-2'-ruthenium tetraminepyridine-aminouridine-CGTAGCA

5'-aminouridine-CGTAGCA (0.3 μm) was dissolved in 0.2M HEPES, 0.8M NaCl buffer, pH 6.8 and degassed on the vacuum line. To a 10 ml conical shaped flask equipped with a stirring bar and septum was slurried Ru(III) tetraaminepyridine chloride (10 μm), in the same buffer. In a separate flask, Zn/Hg amalgam was prepared and dried under reduced pressure and the ruthenium(III) solution transferred (via cannulation) to the Zn/Hg amalgam. The immediate formation of a clear yellow solution ($\lambda_{max}$=406 nm) indicated that the reduced form of the ruthenium had been achieved and the reaction allowed to proceed for 30 minutes. This solution was transferred to the flask containing the amino-modified DNA and the reaction allowed to proceed at room temperature for 24 hours under argon. The reaction mixture was removed from the vacuum line and a 50 fold excess of cobalt EDTA (Kirschner, Inorganic Synthesis (1957), pp 186) added to the solution. The solution was applied to Sephadex G-25 gel filtration column to remove excess ruthenium complex and further purified by reverse phase HPLC as described above. The two ruthenium modified nucleotides were annealed by standard techniques and characterized (see Example 5).

Example 2

Synthesis of Long DNA Duplexes with Electron Transfer Moieties at the 5' Termini In this example, an in vitro DNA amplification technique, PCR (reviewed in Abramson et al., Curr. Op. in Biotech. 4:41–47 (1993)) is used to generate modified duplex DNA by polymerization of nucleotides off modified primer strands (Saiki et al., Science 239:487 (1988)). Two oligonucleotides 18 bases in length and not complementary to each other are synthesized with amino-modification to the 2'-ribose position of the 5' nucleotides, as in example 1.

A series of oligonucleotides of increasing lengths starting at 40 bases are chemically synthesized using standard chemistry. Each of the PCR templates shares a 5' sequence identical to one modified 18 mer. The 3' end of the template oligonucleotide shares a sequence complementary to the other 18 mer.

PCR rapidly generates modified duplex DNA by the catalysis of 5'-3' DNA synthesis off of each of the modified 18 mers using the unmodified strand as a template. One hundred nanomoles of each of the two modified 18mers are mixed in 1 ml of an aqueous solution containing 2,000 units of Taq polymerase, deoxyribonucleoside triphosphates at 0.2M each, 50 mM KCl, 10 mM Tris-Cl, pH 8.8, 1.5 mM $MgCl_2$, 3 mM dithiothreitol and 0.1 mg/ml bovine serum albumin. One femtomole of the template strand 40 bases in length is added to the mixture. The sample is heated at 94°

C. for one minute for denaturation, two minutes at 55° C. for annealing and three minutes at 72° C. for extension. This cycle is repeated 30 times using an automated thermal cycler.

The amplified template sequences with transition metal complexes on both 5' termini are purified by agarose gel electrophoresis and used directly in electron transfer applications.

Example 3

Synthesis of Covalently Bound Electron Transfer Moieties at Internucleotide Linkages of Duplex DNA In this example, alternative backbones to phophodiester linkages of oligonucleotides are employed. Functional groups incorporated into these internucleotide linkages serve as the site for covalent attachment of the electron transfer moieties. These alternate internucleotide linkages include, but are not limited to, peptide bonds, phosphoramidate bonds, phosphorothioate bonds, phosphorodithioate bonds and O-methylphosphoramidate bonds.

The preparation of peptide nucleic acid (PNA) follows literature procedures (See Engholm, supra), with the synthesis of Boc-protected pentaflurophenyl ester of the chosen base (thymidine). The resulting PNA may be prepared employing Merrifield's solid-phase approach (Merrifield, Science, 232:341 (1986)), using a single coupling protocol with 0.1M of the thiminyl monomer in 30% (v/v) DMF in $CH_2Cl_2$. The progress of the reaction is followed by quantiative ninhydrin analysis (Sarin, Anal. Biochem., 117:147 (1981)). The resulting PNA may be modified with an appropriate transition metal complex as outlined in example 1.

The synthesis of phosphoramidate (Beaucage, supra, Letsinger, supra, Sawai, supra) and N-alkylphosphoramidates (Jager, supra) internucleotide linkages follows standard literature procedures with only slight modification (the procedures are halted after the addition of a single base to the solid support and then cleaved to obtain a dinucleotide phosphoramidate). A typical example is the preparation of the phenyl ester of 5'O-isobutyloxycarbonylthymidyl-(3'-5')-5'-amino-5'-deoxythymidine (Letsinger, J. Org. Chem., supra). The dimer units are substituted for standard oligonucleotides at chosen intervals during the preparation of DNA using established automated techniques. Transition metal modification of the modified linkages takes place as described in Example 1.

The synthesis of phosphorothioate and phosphorodithioate (Eckstein, supra, and references within) internucleotide linkages is well documented. A published protocol utilizes an Applied Biosystems DNA synthesizer using a modified β-cyanoethylphosphoramidite cycle that caps after sulphurization with tetraethylthiuram disulfide (TETD) (lyer, J. Org. Chem. 55:4693 (1990)). The phosphorothioate and phosphorodithioate analogs are prepared as dimers and cleaved from the solid support and purified by HPLC (acetonitrile/triethylammonium acetate mobile phase).

Example 4

Synthesis of Two Oligonucleotides each with an electron transfer moiety at the 5' terminus In this example, two oligonucleotides are made which hybridize to a single target sequence, without intervening sequences. One oligonucleotide has an electron donor moiety covalently attached to the 5' terminus, and the other has an electron acceptor moiety covalently attached to the 5' terminus. In this example, the electron transfer species are attached via a uridine nucleotide, but one skilled in the art will understand the present methods can be used to modify any of the nucleotides. In addition, one skilled in the art will recognize that the procedure is not limited to the generation of 8-mers, but is useful in the generation of oligonucleotide probes of varying lengths.

The procedure is exactly as in Example 1, except that the 8-mers generated are not complementary to each other, and instead are complementary to a target sequence of 16 nucleotides. Thus the final annealing step of step 4 of Example 1 is not done. Instead, the two modified oligonucleotides are annealed to the target sequence, and the resulting complex is characterized as in Example 5.

Example 5

Characterization of Modified Nucleic Acids

Enzymatic digestion

The modified oligonucleotides of example 1 were subjected to enzymatic digestion using established protocols and converted to their constituent nucleosides by sequential reaction with phosphodiesterase and alkaline phosphatase. By comparison of the experimentally obtained integrated HPLC profiles and UV-vis spectra of the digested oligonucleotides to standards (including 2'-aminouridine and 2'-aminoadenine), the presence of the amino-modified base at the predicted retention time and characteristic UV-vis spectra was confirmed. An identical procedure was carried out on the transition metal modified duplex DNA and assignments of constituent nucleosides demonstrated single-site modification at the predicted site.

Fluorescent labeled amino-modified oligonucleotides

It has been demonstrated that the fluorochrome, fluorescein isothiocyanate (FITC) is specific for labeling primary amines on modified oligonucleotides while not bonding to amines or amides present on nucleotide bases (Haugland, Handbood of Fluorescent Probes and Research Chemicals, 5th Edition, (1992)). This reaction was carried out using the amino-oligonucleotide synthesized as described in example 1 and on an identical bases sequence without the 2'-amino-ribose group present. Fluorescence spectroscopic measurements were acquired on both these oligonucleotides and the results confirm the presence of the amine on the 5'-terminal ribose ring.

Thermodynamic Melting Curves of Modified Duplex DNA

A well established technique for measuring thermodynamic parameters of duplex DNA is the acquisition of DNA melting curves. A series of melting curves as a function of concentration of the modified duplex DNA was measured via temperature controlled UV-vis (Hewlett-Packard), using techniques well known in the art. These results confirm that hybridization of the amino-modified and transition metal modified DNA had taken place. In addition, the results indicate that the modified DNA form a stable duplex comparable to the stability of unmodified oligonucleotide standards.

Two Dimensional Nuclear Magnetic Resonance (NMR) Spectroscopy

The amino-modified oligonucleotides synthesized as a part of this work were prepared in sufficient quantities (6 micromoles) to permit the assignment of the $^1H$ proton NMR spectra using a 600 MHz Varian NMR spectrometer.

Measurement of the rate of electron transfer

An excellent review of the measurement techniques is found in Winkler et al., Chem. Rev. 92:369–379 (1992). The donor is Ru(bpy)$_2$(NHuridine)im, E$^0$~1 V, and the acceptor is Ru(NH$_3$)$_4$py(NHuridine)im, E$^0$~330 mV. The purified transition metal modified oligonucleotides (U$_{NHRu(bpy)2im}$GCATCGA and U$_{NHRu(NH3)4(py)im}$CGATGCA were annealed by heating an equal molar mixture of the oligonucleotides (30 μmolar: 60 nmoles of DNA in 2 ml buffer) in pH 6.8 (100 mM NaPi, 900 mM NaCl) to 60° C. for 10 minutes and slowly cooling to room temperature over a period of 4 hours. The solution was transferred to an inert atmosphere cuvette equipped with adapters for attachment to a vacuum line and a magnetic stirring bar. The solution was degassed several times and the sealed apparatus refilled repeatedly with Ar gas.

The entire apparatus was inserted into a cuvette holder as part of the set-up using the XeCl excimer-pumped dye laser and data acquired at several wavelengths including 360, 410, 460 and 480 nm. The photoinduced electron transfer rate is 1.6×10$^6$ s$^{-1}$ over a distance of 28 Å.

Example 6

Synthesis of a single stranded nucleic acid labeled with two electron transfer moieties This example uses the basic procedures described earlier to generate two modified oligonucleotides each with an electron transfer moiety attached. Ligation of the two modified strands to each other produces a doubly labeled nucleic acid with any of four configurations: 5' and 3' labeled termini, 5' labeled terminus and internal nucleotide label, 3' labeled terminus and internal nucleotide label, and double internal nucleotide labels. Specifically, the synthesis of an oligonucleotide 24 bases in length with an electron transfer donor moiety on the 5' end and an internal electron transfer moiety is described.

Five hundred nanomoles of each of two 5'-labeled oligonucleotides 12 bases in length are synthesized as detailed above with ruthenium (II) bisbipyridine imidazole on one oligonucleotide, "D" and ruthenium (III) tetraamine pyridine on a second oligonucleotide, "A".

An unmodified oligonucleotide 24 bases in length and complementary to the juxtaposition of oligonucleotide "D" followed in the 5' to 3' direction by oligonucleotide "A" is produced by standard synthetic techniques. Five hundred nanomoles of this hybridization template is added to a mixture of oligonucleotides "A" and "D" in 5 ml of an aqueous solution containing 500 mM Tris-Cl, pH 7.5, 50 mM MgCl$_2$, 50 mM dithiothreitol and 5 mg/ml gelatin. To promote maximal hybridization of labeled oligonucleotides to the complementary strand, the mixture is incubated at 60° C. for 10 minutes then cooled slowly at a rate of approximately 10° C. per hour to a final temperature of 12° C. The enzymatic ligation of the two labeled strands is achieved with T4 DNA ligase at 12° C. to prevent the ligation and oligomerization of the duplexed DNA to other duplexes (blunt end ligation). Alternatively, E. coli DNA ligase can be used as it does not catalyze blunt end ligation.

One hundred Weiss units of T4 DNA ligase is added to the annealed DNA and adenosine triphosphate is added to a final concentration of 0.5 mM. The reaction which catalyzes the formation of a phosphodiester linkage between the 5' terminal phosphate of oligonucleotide "A" and the 3' terminal hydroxyl group of oligonucleotide "D" is allowed to proceed for 18 hours at 12° C. The reaction is terminated by heat inactivation of the enzyme at 75° C. for 10 minutes. The doubly labeled oligonucleotide is separated from the singly labeled oligonucleotides and the complementary unlabeled oligonucleotide by HPLC in the presence of urea as in the previous examples. The doubly labeled oligonucleotide of this example is ideally suited for use as a photoactive gene probe as detailed below.

Example 7

Use of a doubly modified oligonucleotide with electron transfer moieties as a photoactive probe for homologous nucleic acid sequence detection This example utilizes the oligonucleotide 24 mer of example 6 in a unique type of gene-probe assay in which removal of unhybridized probe prior to signal detection is not required. In the assay procedure, a region of the gag gene of human immunodeficiency virus type I (HIV-I) is amplified by the polymerase chain reaction (Saiki et al., Science 239:487–491 (1988)). This region of HIV-I is highly conserved among different clinical isolates.

The amplified target DNA versus controls lacking in HIV-I DNA are added to a hybridization solution of 6×SSC (0.9M NaCl, 0.09M Na citrate, pH 7.2) containing 50 nanomoles of doubly labeled 24 mer probe of example 6. Hybridization is allowed to proceed at 60° C. for 10 minutes with gentle agitation. Detection of electron transfer following laser excitation is carried out as in example 5. Control samples which lack the hybridized probe show negligible electron transfer rates. Probes hybridized to the gag sequence show efficient and rapid electron transfer through the DNA double helix, providing a highly specific, homogeneous and automatable HIV-I detection assay.

A similar homogeneous gene probe assay involves the use of two probes, one an electron donor and the other an electron acceptor, which hybridize with the gag region of HIV-I in a tandem configuration, one probe abutting the other. In this assay, electronic coupling between the two electron transfer moieties depends entirely on hybridization with the target DNA. If appropriate, the electron transfer from one probe to the other is enhanced by the ligation of the juxtaposed ends using T4 DNA ligase as in example 6.

Example 8

Preparation of a Hydroxythiol for Attachment to a Gold Electrode

OH(CH$_2$)$_{16}$OH was purchased from Aldrich and the monoacetate form prepared by slurring the material in dry CH$_2$Cl$_2$. 0.5 equiv. of dimethylaminopyridine was added along with 1.4 equivalents of triethylamine and 1 equivalent of acetic anhydride. The reaction was allowed to proceed for 2 hours and purified by flash chromatography (80:20 hexane:diethyl ether.

The monoacetate compound was converted to the monotosylate-monoacetate using p-TSOCI by literature procedures and then treated with triphenyl methylmercaptan. To remove the monoacetate, the product was dissolved in MeOH (1 mmol, 9 ml), cooled to 0° C., and aqueous solution of NaOH (1 mmol, in 2 ml water) added. The temperature was allowed to rise to room temperature slowly, and the reaction followed by TLC (5% MeOH/CH$_2$Cl$_2$). When the ester was gone the mixture was recooled to 0° C., and acidified with KHSO$_4$ to pH 5–6 using pH paper. The MeOH was evaporated, and the residue was extracted with CH$_2$Cl$_2$ (200 ml), dried (Na$_2$SO$_4$), evaporated and checked via TLC. The material was phosphoroamidited by standard procedures. This material was inserted into the DNA synthesizer and an modified oligonucleotide produced. The phosphoramidited oligonucleotide was modified with a ruthenium complex by adding Ru(bpy)$_2$CO$_3$ followed by imidazole to yield a Ru(bpy)₂im oligonucleotide. The trityl protecting group was removed by dissolving the nucleotide in 200 μl of 0.1M triethylammonium acetate (TEAA) buffer, pH 7.5. 30 μl of 1M silver nitrate solution was added and the mixture vortexed and incubated at room temperature for 30 minutes. 50μ of 1M dithiothritol (DTT) was added, the mixture vortexed and incubated for 15 minutes, at which point it was microcentrifuged for 15 minutes to remove precipitated Ag+DTT. The supernatant was collected and the pellet was washed with 100 μl of TEAA buffer and the solutions pooled. The resulting oligonucleotide was then attached to the gold surface by standard techniques.

Example 9

Synthesis of a single stranded nucleic acid containing both an electron acceptor and an electron donor moiety In order to evaluate the path dependent nature of the electron transfer process through duplex DNA, an oligonucleotide was prepared with an electron donor at the 3' end and an electron acceptor at the 5' end. This multiply-modified oligonucleotide was prepared by synthesizing a derivative with an amine at the 2'-position of the terminal ribose of both ends.

Synthesis of Bis-3',5'-2'-deoxyuridine Oligonucleotides A DMT-2'-N-trifluoroacetyl-protected phosphoroamidite of 2'-amino-2'-deoxyuridine ($U_{NH2}$) was prepared as described earlier and reacted with succinic anhydride. This material was reacted with p-nitrophenol to produce the precursor for the attachment to the controller pore glass (GPG) resin as in FIG. 6A. The modified oligonucleotide were assembled by standard solid phase automated DNA synthesis techniques and the bis-3',5',-2'-amino-2'-deoxyuridine oligonucleotide isolated and characterized by mass spectrometry and HPLC digestion analysis. In addition, the aminoribose oligomers and their complements were reacted with FITC under conditions that favor labeling of primary amines. As expected, only the 2'-amino-2'deoxyribose site was labeled verifying the presence of a primary amine on the DNA. As an example, a 11 base pair sequence was prepared (calc. for $U_{NH2}$CTCCTACACU$_{NH2}$-3229; found 3229.1) and the subsequent digestion map was consistent with the proposed structure. The metal modification of the bis-amino modified oligonucleotide was performed in a similar manner. The new metal-modified oligonucleotides were characterized by fluorescent labelling, enzymatic digestion, and duplex-melting temperature studies.

Thermal denaturing and annealing experiments display similar melting temperatures for both ruthenium and aminoribose oligomers. In addition, the amino-modified duplex DNA has been characterized by 2D NMR. These data confirm that the donors and acceptors are covalently attached to the 2'-amino-2'deoxyribose position and indicate that the DNA structure is unperturbed by the presence of the ruthenium complexes.

We claim:

1. A composition comprising a single-stranded nucleic acid containing at least one electron donor moiety and at least one electron acceptor moiety, wherein said electron donor moiety and said electron acceptor moiety are covalently attached to said nucleic acid, and wherein said electron donor moiety and said electron acceptor moiety are not redox proteins.

2. A composition comprising a single-stranded nucleic acid containing at least one electron donor moiety and at least one electron acceptor moiety, wherein at least one of said electron donor moiety and said electron acceptor moiety is an electrode and the other is an electron transfer moiety which is not a redox protein and which is covalently attached to said nucleic acid.

3. A composition comprising a first single stranded nucleic acid containing at least one electron donor moiety and a second single stranded nucleic acid containing at least one electron acceptor moiety, wherein said electron donor and acceptor moieties are covalently attached to said nucleic acid such that there are no more than seven sigma bonds between each of said electron donor and acceptor moieties and the closest base, and wherein said electron donor moiety and said electron acceptor moiety are not redox proteins.

4. A composition comprising a first single stranded nucleic acid containing at least one electron donor moiety and a second single stranded nucleic acid containing at least one electron acceptor moiety, wherein at least one of said electron donor moiety and said electron acceptor moiety is an electrode, and the other is an electron transfer moiety which is not a redox protein and which is covalently attached to said nucleic acid.

5. A composition according to claim 1, 2, 3 or 4 wherein at least one of said electron acceptor moiety and said electron donor moiety is attached to a terminal base.

6. A composition according to claim 1, 2, 3 or 4 wherein said nucleic acid comprises a ribose-phosphate backbone.

7. A composition according to claim 6 wherein at least one of said electron acceptor moiety and said electron donor moiety is attached to a ribose of said ribose-phosphate backbone.

8. A composition according to claim 1, 2, 3 or 4 wherein said nucleic acid comprises a nucleic acid analog.

9. A composition according to claim 8 wherein said nucleic acid analog comprises a peptide nucleic acid.

10. A composition according to claim 1, 2, 3 or 4 wherein at least one of said electron donor moiety and said electron acceptor moiety is a transition metal complex.

11. A composition according to claim 10 wherein said transition metal complex comprises ruthenium, rhenium, osmium, platinium, copper or iron.

12. A composition according to claim 1, 2, 3 or 4 wherein at least one of said electron donor moiety and said electron acceptor moiety is an organic electron donor or acceptor.

13. A composition according to claim 1 or 3 wherein at least one of said electron donor moiety and said electron acceptor moiety is an electrode.

14. A method of detecting a target sequence in a nucleic acid sample comprising:
   a) hybridizing a single-stranded nucleic acid according to claim 1 or 2 to said target sequence, if present, to form a hybridization complex;
   b) detecting electron transfer between said electron donor and said electron acceptor moieties.

15. A method of detecting a target sequence in a nucleic acid wherein said target sequence comprises a first target domain and a second target domain adjacent to said first target domain, wherein said method comprises:
   a) hybridizing a first nucleic acid containing at least one electron donor moiety to said first target domain;
   b) hybridizing a second nucleic acid containing at least one electron acceptor moiety to said second target domain, wherein said electron donor and electron acceptor moieties are covalently attached to said nucleic acid and are not redox proteins; and
   c) detecting electron transfer between said electron donor and said electron acceptor moieties.

16. A method of detecting a target sequence in a nucleic acid wherein said target sequence comprises a first target domain and a second target domain adjacent to said first target domain wherein said method comprises:
   a) hybridizing a first nucleic acid containing at least one electron donor moiety to said first target domain;
   b) hybridizing a second nucleic acid containing at least one electron acceptor moiety to said second target domain, wherein at least one of said electron donor moiety and said electron acceptor moiety is an electrode, and the other is an electron transfer moiety which is not a redox protein and which is covalently attached to said nucleic acid; and
   c) detecting electron transfer between said electron donor and said electron acceptor moieties.

17. A method according to claim 14, 15 or 16 wherein at least one of said electron acceptor moiety and said electron donor moiety is attached to a terminal base.

18. A method according to claim 14, 15 or 16 wherein said nucleic acid comprises a ribose-phosphate backbone.

19. A method according to claim 18 wherein at least one of said electron acceptor moiety and said electron donor moiety is attached to a ribose of said ribose-phosphate backbone.

20. A method according to claim 14, 15 or 16 wherein said nucleic acid comprises a nucleic acid analog.

21. A composition according to claim 20 wherein said nucleic acid analog comprises a peptide nucleic acid.

22. A method according to claim 14, 15 or 16 wherein at least one of said electron donor moiety and said electron acceptor moiety is a transition metal complex.

23. A composition according to claim 22 wherein said transition metal complex comprises ruthenium, rhenium, osmium, platinium, copper or iron.

24. A method according to claim 14, 15 or 16 wherein at least one of said electron donor moiety and said electron acceptor moiety is an organic electron donor or acceptor.

25. A method according to claim 14, 15 or 16 wherein at least one of said electron donor moiety and said electron acceptor moiety is an electrode.

26. A method for making a single-stranded nucleic acid containing at least one covalently attached electron donor moiety and at least one covalently attached electron acceptor moiety, wherein said donor and acceptor moieties are not redox proteins, said method comprising:
   a) optionally attaching at least one nucleoside to a solid support to form a nascent nucleic acid;
   b) attaching a first modified nucleoside to said solid support or said nascent nucleic acid;
   c) attaching at least one additional nucleoside to said first modified nucleoside;
   d) attaching a second modified nucleoside to said nascent nucleic acid;
   e) optionally attaching at least one additional nucleoside to said nascent nucleic acid; and
   f) covalently attaching an electron donor moiety and an electron acceptor moiety to said modified nucleosides to form said single stranded nucleic acid.

27. A method for making a composition comprising a first single stranded nucleic acid containing at least one electron donor moiety and a second single stranded nucleic acid containing at least one electron acceptor moiety, wherein said electron donor and acceptor moieties are covalently attached to said nucleic acid such that there are no more than seven sigma bonds between each of said electron donor and acceptor moieties and the closest base, and wherein said electron donor moiety and said electron acceptor moiety are not redox proteins, said method comprising:
   a) making said first nucleic acid by:
      i) optionally attaching at least one nucleoside to a solid support to form a nascent first nucleic acid;
      ii) attaching a first modified nucleoside to said solid support or said nascent first nucleic acid;
      iii) attaching at least one additional nucleoside to said first modified nucleoside;
      iv) attaching a second modified nucleoside to said nascent first nucleic acid;
      v) optionally attaching at least one additional nucleoside to said nascent first nucleic acid;
   b) making said second nucleic acid by:
      i) optionally attaching at least one nucleoside to a solid support to form a nascent second nucleic acid;
      ii) attaching a first modified nucleoside to said solid support or said second nascent nucleic acid;
      iii) attaching at least one additional nucleoside to said first modified nucleoside
      iv) attaching a second modified nucleoside to said nascent second nucleic acid;
      v) optionally attaching at least one additional nucleoside to said nascent second nucleic acid; and
   c) covalently attaching an electron donor moiety and an electron acceptor moiety to said modified nucleosides.

* * * * *